(12) United States Patent
Bahulekar et al.

(10) Patent No.: US 9,839,628 B2
(45) Date of Patent: Dec. 12, 2017

(54) COMPOSITIONS AND METHODS FOR PREVENTING STERNAL WOUND INFECTIONS

(75) Inventors: Raman Bahulekar, Kandall Park, NJ (US); Arikha Moses, New York, NY (US); Satish Pulapura, Bridgewater, NJ (US); William C. McJames, II, Hillsborough, NJ (US); Fatima Buevich, Highland Park, NJ (US)

(73) Assignee: TYRX, Inc., Monmouth Junction, NJ (US)

( * ) Notice: Subject to any disclaimer, the term of this patent is extended or adjusted under 35 U.S.C. 154(b) by 0 days.

(21) Appl. No.: 12/791,586

(22) Filed: Jun. 1, 2010

(65) Prior Publication Data

US 2011/0294760 A1 Dec. 1, 2011

Related U.S. Application Data

(60) Provisional application No. 61/460,743, filed on Jun. 1, 2009.

(51) Int. Cl.
| A61K 31/445 | (2006.01) |
| A61K 31/43 | (2006.01) |
| A61K 9/16 | (2006.01) |
| A61K 31/496 | (2006.01) |
| A61K 31/65 | (2006.01) |

(52) U.S. Cl.
CPC ............ *A61K 31/43* (2013.01); *A61K 9/1647* (2013.01); *A61K 31/496* (2013.01); *A61K 31/65* (2013.01)

(58) Field of Classification Search
None
See application file for complete search history.

(56) References Cited

U.S. PATENT DOCUMENTS

| RE3,716 E | 11/1869 | Hall |
| RE3,779 E | 12/1869 | Jenkins |
| 4,209,607 A | 6/1980 | Shalaby et al. |
| 4,272,625 A | 6/1981 | McIntyre et al. |
| 4,355,132 A | 10/1982 | East et al. |
| 4,387,210 A | 6/1983 | Katoh et al. |
| 4,428,932 A | 1/1984 | Overell |
| 4,555,566 A | 11/1985 | Arita et al. |
| 4,638,045 A | 1/1987 | Kohn et al. |
| 4,642,104 A | 2/1987 | Sakamoto et al. |
| 4,709,004 A | 11/1987 | Dai |
| 5,099,060 A | 3/1992 | Kohn et al. |
| 5,159,013 A | 10/1992 | Takida et al. |
| 5,185,424 A | 2/1993 | Casagrande et al. |
| 5,216,115 A | 6/1993 | Kohn et al. |
| 5,317,077 A | 5/1994 | Kohn et al. |
| 5,505,952 A | 4/1996 | Jiang et al. |
| 5,573,553 A | 11/1996 | McBride et al. |
| 5,587,507 A | 12/1996 | Kohn et al. |
| 5,658,995 A | 8/1997 | Kohn et al. |
| 5,670,602 A | 9/1997 | Kohn et al. |
| 6,048,521 A | 4/2000 | Kohn et al. |
| 6,120,491 A | 9/2000 | Kohn et al. |
| 6,284,862 B1 | 9/2001 | Kohn et al. |
| 6,319,492 B1 | 11/2001 | Kohn et al. |
| 6,475,477 B1 | 11/2002 | Kohn et al. |
| 6,503,538 B1 | 1/2003 | Chu et al. |
| 6,602,497 B1 | 8/2003 | Kohn et al. |
| 6,720,402 B2 | 4/2004 | Langer et al. |
| 6,852,308 B2 | 2/2005 | Kohn et al. |
| 7,056,493 B2 | 6/2006 | Kohn et al. |
| 7,202,325 B2 | 4/2007 | Pacetti et al. |
| 7,271,234 B2 | 9/2007 | Kohn et al. |
| 7,301,001 B2 | 11/2007 | Hossainy et al. |
| 7,361,726 B2 | 4/2008 | Pacetti et al. |
| 7,419,504 B2 | 9/2008 | Hossainy |
| 2002/0151668 A1 | 10/2002 | James et al. |
| 2003/0138488 A1 | 7/2003 | Kohn et al. |
| 2003/0216307 A1 | 11/2003 | Kohn et al. |
| 2004/0254334 A1 | 12/2004 | James et al. |
| 2005/0013793 A1 | 1/2005 | Beckman et al. |

(Continued)

FOREIGN PATENT DOCUMENTS

| EP | 0051934 A1 | 5/1982 |
| EP | 0322788 A2 | 7/1989 |

(Continued)

OTHER PUBLICATIONS

PR Newswire (Ceremed's OSTENE® Stops Bone Bleeding Without Added Risk of Surgical Infection, New Study Finds—published Feb. 5, 2008).*
PR Newswire (Ceremed's OSTENE® Improves Bone Fusion and Healing After Surgery, New Study Shows—published May 13, 2008).*
European Search Report for Application No. EP09815387 dated Jan. 14, 2013.
Canadian Office Action for Application No. 2,764,134 dated Nov. 22, 2012.

(Continued)

*Primary Examiner* — Craig Ricci

(74) *Attorney, Agent, or Firm* — Sorell Lenna & Schmidt, LLP

(57) ABSTRACT

The invention generally relates to compositions and methods for preventing sternal wound infections, such as mediastinitis. In certain embodiments, the invention provides an antimicrobial composition including at least one bioresorbable polymer, such as a tyrosine-derived polyesteramide, and at least one antimicrobial agent, in which the composition is adapted to be topically applied to an esophageal perforation in a subject or a median sternotomy incision site in the subject, and in which the at least one antimicrobial agent is present in an amount effective to inhibit development of mediastinitis in the subject.

18 Claims, 2 Drawing Sheets

(56) References Cited

U.S. PATENT DOCUMENTS

| | | |
|---|---|---|
| 2005/0165203 A1 | 7/2005 | Kohn et al. |
| 2005/0169968 A1 | 8/2005 | Elmaleh et al. |
| 2005/0177118 A1 | 8/2005 | Hoganson et al. |
| 2005/0260237 A1 | 11/2005 | Byun et al. |
| 2005/0265960 A1 | 12/2005 | Pacetti et al. |
| 2005/0288481 A1 | 12/2005 | DesNoyer et al. |
| 2006/0034888 A1 | 2/2006 | Pacetti et al. |
| 2006/0115449 A1 | 6/2006 | Pacetti |
| 2006/0173065 A1 | 8/2006 | Bezwada |
| 2006/0177480 A1 | 8/2006 | Sung et al. |
| 2006/0193891 A1 | 8/2006 | Richard |
| 2007/0009565 A1 | 1/2007 | Pacetti et al. |
| 2007/0020312 A1 | 1/2007 | DesNoyer et al. |
| 2007/0135355 A1 | 6/2007 | Bezwada |
| 2007/0198040 A1* | 8/2007 | Buevich ............... A61F 2/0063 606/151 |
| 2007/0202147 A1 | 8/2007 | Kleiner et al. |
| 2007/0243256 A1 | 10/2007 | Kleiner et al. |
| 2007/0281031 A1 | 12/2007 | Yang |
| 2008/0014241 A1 | 1/2008 | DesNoyer et al. |
| 2008/0057127 A1 | 3/2008 | Bezwada |
| 2008/0095918 A1 | 4/2008 | Kleiner et al. |
| 2008/0112999 A1 | 5/2008 | Baluca |
| 2008/0132922 A1 | 6/2008 | Buevich et al. |
| 2008/0175882 A1 | 7/2008 | Trollsas et al. |
| 2008/0241212 A1* | 10/2008 | Moses ....................... A61F 2/12 424/423 |
| 2008/0243049 A1 | 10/2008 | Hardy |
| 2009/0088548 A1 | 4/2009 | Moses et al. |
| 2010/0074940 A1 | 3/2010 | Schwartz et al. |
| 2010/0129417 A1 | 5/2010 | Moses et al. |
| 2010/0167992 A1 | 7/2010 | Schwartz et al. |

FOREIGN PATENT DOCUMENTS

| | | |
|---|---|---|
| EP | 0413375 A1 | 2/1991 |
| EP | 0856558 A1 | 8/1998 |
| EP | 0959091 A1 | 11/1999 |
| EP | 1229065 A1 | 8/2002 |
| JP | 57108129 A | 6/1982 |
| JP | 2000501139 A | 2/2000 |
| JP | 2008500387 A | 1/2008 |
| JP | 2010530921 A | 9/2010 |
| WO | 199719996 A1 | 6/1997 |
| WO | 9952962 A1 | 10/1999 |
| WO | 0149249 A2 | 7/2001 |
| WO | 0149311 A1 | 7/2001 |
| WO | 03091337 A1 | 11/2003 |
| WO | 2005068532 A1 | 7/2005 |
| WO | 2007028244 A1 | 3/2007 |
| WO | 2007098889 A1 | 9/2007 |
| WO | 2008112833 A1 | 9/2008 |
| WO | WO 2008/157777 * 12/2008 ............... A61F 2/00 |  |

OTHER PUBLICATIONS

Extended European Search Report for Application No. EP10783928 dated Jun. 17, 2013.
Australian Examination Report for Application No. 2009292949 dated Sep. 26, 2013.
Brocchini et al., 1997, J. Amer. Chem. Soc. 119:4553-4554.
Carson et al., J Am Coll Cardiol, 40:418-423, 2002.
Clinical Orthopeadics &Rel. Res. 357: 219-228, 1998.
Crabtree et al., Semin Thorac Cardiovasc Surg., 16(1):53-61, 2004.
Department of Health and Human Services, 2007, vol. 72, No. 162.
Elias, et al. 1981 Makromol. Chem. 182:681-686.
Fakin et al., Infect Control Hosp Epidemiol 28(6):655-660, 2007.
Higashi et al., 1983, J. Polym. Sci.: Polym. Chem. Ed. 21 :3241-3247.
Higashi et al., 1983, J. Polym. Sci.: Polym. Chem. Ed. 21:3233-3239.
Higashi et al., 1986, J. Polym. Sci.: Polym. Chem. Ed. 24:97-102.
Higashi et al., 1986, J. Polym. Sci: Polym. Chem. Ed. 24:589-594.
Hollenbeak et al. Infection Control and Hospital Epidemiology, 23(4): 177, 2002.
Hollenbeak et al., Chest, 118:397-402, 2000.
Hooper et al., 1998, J. Biomed. Mat. Res. 41:443-454.
Moore et al., 1990, Macromol. 23:65-70.
Ogata et al., 1981, Polym. J.,13:989-991.
Pulapura & Kohn, 1992, Biopolymers 32:41 1-417.
Pulapura et al., 1990, Biomaterials 11:666-678.
Rahmanian et al., Am J Cardiol, 100(11):1702-1708, 2007.
Tanaka et al. 1982, Polym. J. 14:643-648.
Yasuda et al., 1983, J. Polym. Sci: Polym. Chem. Ed., 21:2609-2616.
Yokoe et al., Emerging Infectious Diseases, 10(11):1924-1930, 2004.
International Search Report for Application No. PCT/US09/57860 dated Jan. 13, 2010.
U.S. Appl. No. 60/375,846, filed Apr. 24, 2002.
JP Office Action for Application No. 2011-528070 dated Dec. 25, 2013.
EP Office Action for Application No. 10783928.4-1455 dated Feb. 10, 2014.
Australian Office Action for Application No. 2010256750 dated Dec. 17, 2013.

\* cited by examiner

COMPOSITIONS AND METHODS FOR PREVENTING STERNAL WOUND INFECTIONS

CROSS-REFERENCE TO RELATED APPLICATIONS

This application claims the benefit of U.S. Provisional patent application Ser. No. 61/460,743, filed Jun. 1, 2009, which is herein incorporated by reference in its entirety for all purposes.

BACKGROUND

Mediastinitis is an infection that results in swelling and inflammation of the area between the lungs containing the heart, large blood vessels, trachea, esophagus, thymus gland, lymph nodes, and connective tissues. Mediastinitis is a life-threatening condition with an extremely high mortality rate if recognized too late or treated improperly. Sternotomy wounds become infected in about 0.5% to about 9% of open-heart procedures and have an associated mortality rate of about 8% to about 15% despite flap closure. The rate of deep sternal wound infection (bone and mediastinitis) associated with median sternotomy ranges from about 0.5% to about 5% and the associated mortality rate is as high as 22% independent of the type of surgery performed.

Mediastinitis is classified as either acute or chronic. Chronic sclerosing (or fibrosing) mediastinitis results from long-standing inflammation of the mediastinum, leading to growth of acellular collagen and fibrous tissue within the chest and around the central vessels and airways. Acute mediastinitis usually results from esophageal perforation or median sternotomy.

An esophageal perforation is a hole in the esophagus, the tube through which food passes from the mouth to the stomach. An esophageal perforation allows the contents of the esophagus to pass into the mediastinum, the surrounding area in the chest, and often results in infection of the mediastinum, i.e., mediastinitis. For patients with an early diagnosis, e.g., less than 24 hours, and a surgery that is accomplished within 24 hours, the survival rate is about 90%. However, that rate drops to about 50% when treatment is delayed.

A median sternotomy is a surgical procedure in which a vertical inline incision is made along the sternum, after which the sternum itself is divided, or cracked. This procedure provides access to the heart and lungs for further surgical procedures such as a heart transplant, correction of congenital heart defects, or coronary artery bypass surgery. After the surgery has been completed, the sternum is usually closed with the assistance of wires or metal tapes. The sternal bony edges and gaps are subsequently covered and filled with a haemostatic agent. The most commonly used haemostatic agent is bone wax (bee's wax), despite the fact that bone wax has been reported to enhance infection, causes a foreign body reaction, and inhibits bone growth (Rahmanian et al., Am J Cardiol, 100(10:1702-1708, 2007; Fakin et al., Infect Control Hosp Epidemiol 28(6):655-660, 2007; and Crabtree et al., Semin Thorac Cardiovasc Surg., 16(1): 53-61, 2004).

The wound site, sternum and/or internal cavity can be contaminated with bacteria at any time during the surgery and closure. Whereas superficial sternal wound infection may not in and of itself be associated with high mortality rates, these infections can track to the bony sternum itself and cause osteomyelitis. Further tracking of infection into the mediastinum results in mediastinitis. Haemostatic agents such as bone wax are commonly employed to provide a physical barrier to entry of bacteria into and through the sternum, however, their inflammatory properties may actually enhance bacterial growth. More effective treatments should employ pharmacological as well as physical methods for preventing contamination of the wound bed.

Although prophylactic antibiotics are the standard of care prior to most surgical procedures, IV antibiotics alone have not been very effective at reducing the incidence of sternal wound infection and mediastinitis. Also, there has been a growing concern of antibiotic resistance due to the absence of high local concentration at the sternal wound site (Carson et al., J Am Coll Cardiol, 40:418-423, 2002). Patients that develop deep chest surgical site infection incur an average cost of $20,927 more than non-infected patients, and incur an average length of hospital stay of twenty-seven days compared to five or six days for non-infected patients.

Beginning in 2009, costs associated with treating acute mediastinitis will not be covered by Medicare. See Centers for Medicare & Medicaid Services Inpatient Prospective Payment System published in the Federal Register (Department of Health and Human Services, 2007, Vol. 72, No. 162) on Aug. 22, 2007.

There is, therefore, a need for compositions and methods for preventing mediastinitis.

SUMMARY OF THE INVENTION

The invention provides a topical composition including at least one antibiotic agent for application to an incision site in a patient having undergone a median sternotomy or other procedure in which the sternum is compromised. As used herein, topical refers to a formulation that is applied into, on top of, or in the interstices of a surface of a subject, i.e., application to an internal surface or an external surface of a subject. The surface can be a surface of an internal bone, an edge of a surgically cut internal bone, a surface of an internal organ, a surface of an internal muscle, or a surface of an incision site. In particular, topical includes formulated for application to the inside of the margins of a median sternotomy, i.e., application to the sternal bony edges and gaps after a median sternotomy has been performed. Topical also include application to a surface of an esophageal perforation. Topical also includes application to the epidermis. Compositions of the invention may be made of any appropriate material and are preferably formulated as a paste, putty, cream, ointment, foam, or gel. Application of compositions of the invention in, for example, cardiac surgery, greatly reduces infection leading to mediastinitis.

An aspect of the invention provides an antimicrobial composition including at least one bioresorbable polymer, such as a tyrosine-derived polyesteramide and at least one antimicrobial agent, in which the composition is formulated for topical application to an esophageal perforation in a subject or a median sternotomy incision site in the subject, and in which the antimicrobial agent is present in an amount effective to inhibit bacterial colonization of the site and/or development of mediastinitis, a sternal wound infection, or a deep wound infection in the subject. In preferred embodiments, the composition is applied in between and on top of the sternum of a subject after closure using standard techniques. Topical formulations of such compositions include, but are not limited to, a putty, a paste, a gel, a foam, an ointment, or a cream. In certain embodiments, the composition further includes a binder.

Certain embodiments of these compositions further include an osteoinductive agent. Other embodiments of these compositions further include an osteoconductive agent. Exemplary bone-growth promoting substances include calcium phosphate, demineralized bone matrix, collagen, or hydroxyapatite.

In certain embodiments of these compositions, the binder is a polyalkyelene oxide, for example polyethylene glycol (PEG) or polypropylene glycols, including copolymers thereof. In particular embodiments, the binder is PEG 400. In other embodiments, the binder is a block copolymer of polyethylene oxide (PEO) and polypropylene oxide (PPO), such as Pluronic® triblock PEO/PPO copolymers available from BASF. In certain embodiments, the compositions herein are partially bioresorbable. In other embodiments, the compositions are completely bioresorbable.

Antimicrobial agents can include antibiotics, antiseptics, and disinfectants that are non-toxic and employable directly to internal organs. Exemplary antibiotic agents include tetracyclines, penicillins, macrolides, rifampin and combinations thereof. In certain embodiments, the composition includes a combination of antibiotic agents, such as minocycline and rifampin.

In certain embodiments, compositions of the invention include a tyrosine-derived polyesteramide and at least one additional polymer selected from the group consisting of polylactic acid, polyglycolic acid, poly(L-lactide) (PLLA), poly(D,L-lactide) (PLA) polyglycolic acid [polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL), poly(glycolide-co-caprolactone) (PGA/PCL), poly(oxa)esters, polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT), polyhydroxybutyrate, poly(phosphazene), polyphosphate ester), poly(amino acid), polydepsipeptides, polyiminocarbonates, poly[(97.5% dimethyl-trimethylene carbonate)-co-(2.5% trimethylene carbonate)], poly(orthoesters), tyrosine-derived polycarbonates, tyrosine-derived polyiminocarbonates, tyrosine-derived polyphosphonates, polyethylene oxide, polyalkylene oxides, and hydroxypropylmethylcellulose.

Another aspect of the invention provides a method of preventing mediastinitis, sternal wound infections, or deep wound infections in a subject, for example, a human, in which one applies an antimicrobial composition including a polymer and at least one antimicrobial agent to an esophageal perforation in a subject or a median sternotomy incision site in the subject, in which the at least one antimicrobial agent is present in an amount effective to prevent development of mediastinitis, sternal wound infections, or deep wound infections, in the subject. By "preventing" mediastinitis, we mean substantially inhibiting microbial growth (e.g. by providing sufficient amounts of antimicrobial agents, as described herein, to inhibit bacterial growth) such that the incidence of mediastinitis is significantly reduced, for example by at least about 10%, for example, at least about 10%, at least about 20%, at least about 30%, at least about 40%, at least about 50%, at least about 60%, at least about 70%, at least about 80%, at least about 90%, or at least about 95%.

In certain embodiments of the method, the composition further includes a binder, for example polyethylene glycol (PEG). In particular embodiments, the PEG is PEG 400. In other embodiments of the method, the composition further includes an osteoinductive agent. In other embodiments of the method, the composition further includes an osteoconductive agent. In certain embodiments of the method, the polymer is a tyrosine-derived polyesteramide. In certain embodiments of the method, the polymer is a blend of at least two polymers. In certain embodiments of the method, the polymer is a blend of a tyrosine-derived polyesteramide and at least one additional polymer selected from the group consisting of: polylactic acid, polyglycolic acid, poly(L-lactide) (PLLA), poly(D,L-lactide) (PLA) polyglycolic acid [polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL), poly(glycolide-co-caprolactone) (PGA/PCL), poly(oxa)esters, polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT), polyhydroxybutyrate, poly(phosphazene), poly(phosphate ester), poly(amino acid), polydepsipeptides, polyiminocarbonates, poly[(97.5% dimethyl-trimethylene carbonate)-co-(2.5% trimethylene carbonate)], poly(orthoesters), tyrosine-derived polycarbonates, tyrosine-derived polyiminocarbonates, tyrosine-derived polyphosphonates, polyethylene oxide, polyalkylene oxides, and hydroxypropylmethylcellulose.

In certain embodiments of the method, the polymer composition can be delivered to the patient in various forms. In certain embodiments, the composition is formulated as a paste. In other embodiments, the composition is formulated as a putty. Other exemplary formulations include a foam, a gel, an ointment, or a cream. In certain embodiments, the composition is partially bioresorbable. In other embodiments, the composition is completely bioresorbable. In other embodiments, the composition is bioresorbable and remodeled.

Another aspect of the invention provides a method of preventing mediastinitis in a subject, in which a putty comprising a tyrosine-derived polyesteramide, a binder, and at least one antimicrobial agent is applied to an esophageal perforation in a subject or a sternotomy in the subject, in which the at least one antimicrobial agent is present in an amount effective to prevent development of mediastinitis in the subject.

DETAILED DESCRIPTION

Figure 1:
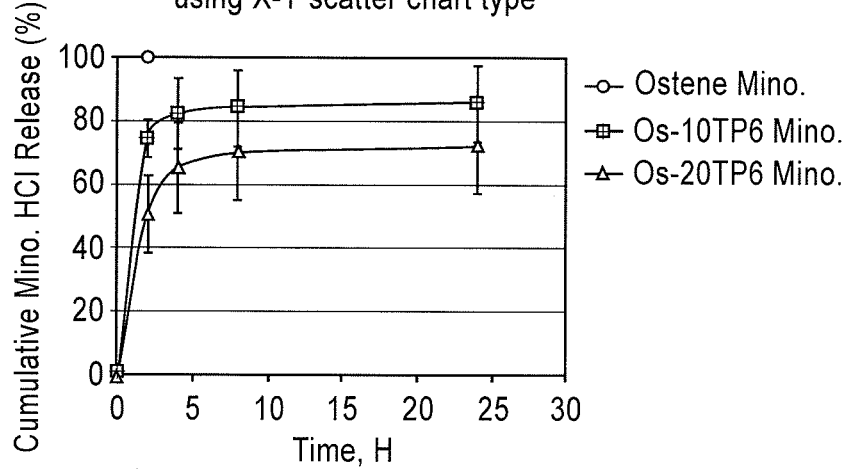
FIG. 1 illustrates the rate of minocycline release from Ostene® formulations.

The invention generally relates to compositions and methods for preventing sternal wound infections, deep wound infections, or mediastinitis. Mediastinitis is an infection caused by bacteria or fungi. The infection results in swelling and irritation (inflammation) of the area between the lungs (the mediastinum). Bacterial organisms and fungal organisms refer to all genuses and species of bacteria and fungi, including, for example, all spherical, rod-shaped and spiral bacteria. Exemplary bacteria are *staphylococci* (e.g., *Staphylococcus epidermidis* and *Staphylococcus aureus*), *Enterrococcus faecalis*, *Pseudomonas aeruginosa*, *Escherichia coli*, other gram-positive bacteria, and gram-negative *bacilli*. An exemplary fungus is *Candida albicans*. Although mediastinitis is often polymicrobial, *staphylococci* are the most common bacteria colonized from infected patients.

In certain embodiments, the invention provides an antimicrobial composition including at least one bioresorbable polymer, such as a tyrosine-derived polyesteramide and at least one antimicrobial agent, in which the composition is formulated for topical application to an esophageal perforation in a subject or a median sternotomy incision site in the subject, and in which the at least one antimicrobial agent is present in an amount effective to sterilize the sternal wound site, i.e. prevent bacterial colonization of the wound site. In certain embodiments, the composition includes a binder.

As used herein, topical refers to a formulation that is applied into, on top of, or in the interstices of a surface of a subject, i.e., application to an internal surface or an external surface of a subject. The surface can be a surface of an internal bone, an edge of a surgically cut internal bone, a surface of an internal organ, a surface of an internal muscle, or a surface of an incision site. In particular, topical includes formulations for application to the inside of the margins of a median sternotomy, i.e., application to the sternal bony edges and gaps after a median sternotomy has been performed. Topical also include application to a surface of an esophageal perforation. Topical also includes application to the epidermis.

Antimicrobial Agents

Antimicrobial agents include antibiotics, antiseptics, and disinfectants. In certain embodiments, the antimicrobial composition includes only one of these agents. In other embodiments, the antimicrobial composition includes mixtures and combinations of these agents, for example, an antibiotic and an antiseptic, multiple disinfectants, or multiple antibiotics, or multiple antibiotics and multiple disinfectants, etc. In certain embodiments, the antimicrobial agents are soluble in organic solvents such as alcohols, ketones, ethers, aldehydes, acetonitrile, acetic acid, methylene chloride and chloroform.

Non-limiting examples of classes of antibiotics that can possibly be used include tetracyclines (e.g. minocycline), rifamycins (e.g. rifampin), macrolides (e.g. erythromycin), penicillins (e.g. nafeillin), cephalosporins (e.g. cefazolin), other β-lactam antibiotics (e.g. imipenem, aztreonam), aminoglycosides (e.g. gentamicin), chloramphenicol, sufonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and β-lactam inhibitors (e.g. sulbactam).

Non-limiting examples of specific antibiotics that can be used include minocycline, rifampin, erythromycin, azithromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, novobiocin, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, bacitracin, clindamycin, daptomycin, lincomycin, linezolid, metronid, polymyxin, rifaximin, vancomycin, triclosan, chlorhexidine, sirolimus, everolimus, and nystatin. Other examples of antibiotics, such as those listed in Sakamoto et al. (U.S. Pat. No. 4,642,104), will readily suggest themselves to those of ordinary skill in the art.

Minocycline is a semi-synthetic antibiotic derived from tetracycline. It is primarily bacteriostatic and exerts its antimicrobial effect by inhibiting protein synthesis. Minocycline is commercially available as the hydrochloride salt which occurs as a yellow, crystalline powder and is soluble in water and slightly soluble in organic solvents including alcohols, ketones, ethers, aldehydes, acetonitrile, acetic acid, methylene chloride and chloroform. Minocycline is active against a wide range of gram-positive and gram-negative organisms.

Rifampin is a semi-synthetic derivative of rifamycin B, a macrocyclic antibiotic compound produced by the mold *Streptomyces mediterranic*. Rifampin inhibits bacterial DNA-dependent RNA polymerase activity and is bactericidal in nature. Rifampin is commercially available as a red-brown crystalline powder and is very slightly soluble in water and freely soluble in acidic aqueous solutions and organic solutions including alcohols, ketones, ethers, aldehydes, acetonitrile, acetic acid, methylene chloride and chloroform. Rifampin possesses a broad spectrum activity against a wide range of gram-positive and gram-negative bacteria.

Novobiocin is an antibiotic obtained from cultures of *Streptomyces niveus* or *S. spheroides*. Novobiocin is usually bacteriostatic in action and appears to interfere with bacterial cell wall synthesis and inhibits bacterial protein and nucleic acid synthesis. The drug also appears to affect stability of the cell membrane by complexing with magnesium. Novobiocin sodium is freely soluble in water and alcohol. Novobiocin is available from The Upjohn Company, Kalamazoo, Mich.

Erythromycin is a macrolide antibiotic produced by a strain of *Streptomyces erythreaus*. Erythromycin exerts its antibacterial action by inhibition of protein synthesis without affecting nucleic acid synthesis. It is commercially available as a white to off-white crystal or powder slightly soluble in water and soluble in organic solutions including alcohols, ketones, ethers, aldehydes, acetonitrile, acetic acid, methylene chloride and chloroform. Erythromycin is active against a variety of gram-positive and gram-negative bacteria.

Nafeillin is a semi-synthetic penicillin that is effective against both penicillin-G-sensitive and penicillin-G-resistant strains of *Staphylococcus aureus* as well as against *pneumococcus*, beta-hemolytic *streptococcus*, and alpha *streptococcus* (viridans *streptococci*). Nafcillin is readily soluble in both water and organic solutions including alcohols, ketones, ethers, aldehydes, acetonitrile, acetic acid, methylene chloride and chloroform.

Examples of antiseptics and disinfectants are hexachlorophene, cationic bisiguanides (e.g. chlorhexidine, cyclohexidine) iodine and iodophores (e.g. povidone iodine), para-chloro-meta-xylenol, triclosan, furan medical preparations (e.g. nitrofurantoin, nitrofurazone), methenamine, aldehydes (glutaraldehyde, formaldehyde) and alcohols. Other examples of antiseptics and disinfectants will readily suggest themselves to those of ordinary skill in the art.

Hexachlorophene is a bacteriostatic antiseptic cleansing agent that is active against *staphylococci* and other gram-positive bacteria. Hexachlorophene is soluble in both water and organic solutions including alcohols, ketones, ethers, aldehydes, acetonitrile, acetic acid, methylene chloride and chloroform.

These antimicrobial agents can be used alone or in combination of two or more of them. The antimicrobial agents can be dispersed throughout the polymer or in some portion of the polymer, e.g., tyrosine-derived polyesteramides. The amount of each antimicrobial agent used varies to some extent, but is at least of an effective concentration to prevent development of mediastinitis in a subject.

Tyrosine-Derived Polyesteramide

Non-limiting examples of tyrosine-derived polyesteramides include alternating A-B type copolymers consisting of a diphenol component and a dicarboxylic acid component. The dicarboxylic acids allow for variation in the polymer backbone while the diphenols contain a moiety for appending and varying a pendent chain.

The polyesteramides are based upon certain tyrosine-derived monomers, which are co-polymerized with a variety of dicarboxylic acids. The tyrosine-derived monomer can be thought of as a desaminotyrosyl tyrosine dipeptide in which the pendant carboxyl group of the tyrosine moiety has been esterified. The structure of one example of a suitable tyrosine-derived monomer is shown in Formula 1.

Formula 1

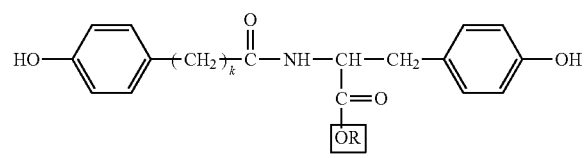

k = 1,2

In Formula 1, R is selected from the group consisting of: a straight or branched chain alkyl group containing up to 18 carbon atoms, an alkylaryl group containing up to 18 carbon atoms, a straight or branched chain alkyl group containing up to 18 carbon atoms in which one or more carbon atoms is substituted by an oxygen, and an alkylaryl group containing up to 18 carbon atoms in which one or more carbon atoms is substituted by an oxygen.

In certain embodiments, R is a straight or branched chain alkyl group containing 2-8 carbon atoms. In other embodiments, R is selected from the group consisting of: methyl, ethyl, propyl, butyl, isobutyl, sec-butyl, hexyl, octyl, 2-(2-ethoxyethoxy)ethanyl, dodecanyl, and benzyl. In still other embodiments, R is selected from the group consisting of: ethyl, hexyl, and octyl. In other embodiments, R is ethyl and k is 2.

One non-limiting example of a class of polyesteramides suitable for use in the present invention is formed by polymerizing the tyrosine-derived monomers of Formula 1 with the diacarboxylic acids of Formula 2.

Formula 2

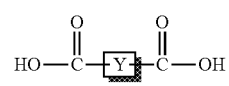

In Formula 2, Y is a saturated or unsaturated, substituted or unsubstituted alkylene, arylene, and alkylarylene group containing up to 18 carbon atoms. The substituted alkylene, arylene, and alkylarylene groups may have backbone carbon atoms replaced by N, O, or S, or may have backbone carbon atoms replaced by keto, amide, or ester linkages. Y can be selected so that the dicarboxylic acids are either important naturally-occurring metabolites or highly biocompatible compounds. In certain embodiments, dicarboxylic acids include the intermediate dicarboxylic acids of the cellular respiration pathway known as the Krebs Cycle. These dicarboxylic acids include α-ketoglutaric acid, succinic acid, fumaric acid, malic acid and oxaloacetic acid, for which Y is —$CH_2$—$CH_2$—C(=O)—, —$CH_2$—$CH_2$—, —CH=CH—, —$CH_2$—CH(—OH)—, and —$CH_2$—C(=O)—, respectively.

In particular embodiments, Y in Formula 2 is a straight chain alkylene group having 2-8 carbons. In particular embodiments, Formula 2 is one of the following dicarboxylic acid, succinic acid, glutaric acid, diglycolic acid, adipic acid, 3-methyladipic acid, suberic acid, dioxaoctadioic acid and sebacic acid.

When polymerized, the tyrosine-derived monomers of Formula 1 and the dicarboxylic acids of Formula 2 give rise to polyesteramides that can be represented by Formula 3.

Formula 3

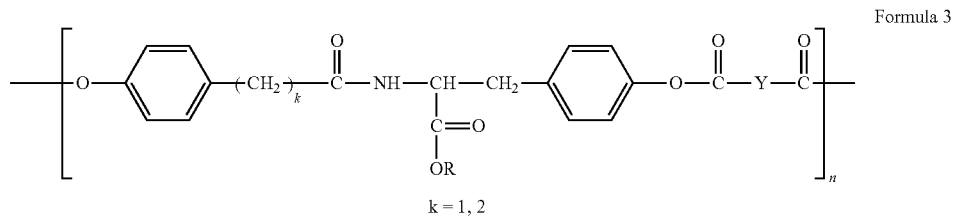

k = 1, 2 where R and Y are as described above. In this formula, as in other formulas herein, an "n" outside brackets or parentheses, and having no specified value, has its conventional role in the depiction of polymer structures. That is, "n"

represents a large number, the exact number depending on the molecular weight of the polymer. This molecular weight will vary depending upon the conditions of formation of the polymer.

A particular subset of the polyesteramides of Formula 3 is the subset where k=2 and both R and Y are straight chain alkyl groups. This polyesteramide subset can be represented by Formula 4.

ethyl ester, succinic acid, and desaminotyrosyl tyrosine. The monomer desaminotyrosyl tyrosine (referred to herein as "DT") is the same as desaminotyrosyl tyrosine ethyl ester except that it contains a pendant free carboxylic acid group rather than the pendant ethyl ester of desaminotyrosyl tyrosine ethyl ester.

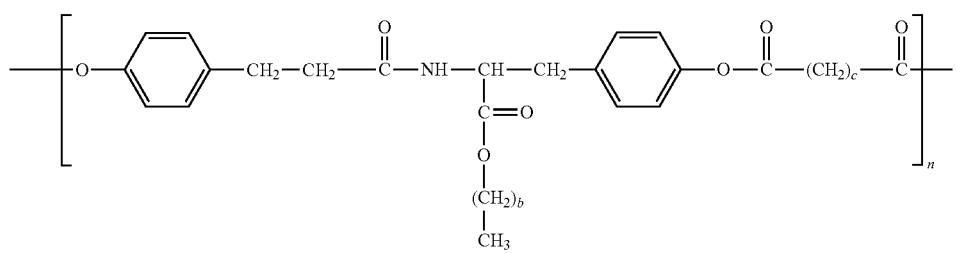

Formula 4

In Formula 4, b=1-17 and c=1-18. In certain embodiments, b=1-7 and c=2-8.

A polyesteramide for use in the present invention is the polyesteramide of Formula 4 where b=1 and c=2. This polyesteramide is referred to herein as p(DTE succinate). This name illustrates the nomenclature used herein, in which the names of polyesteramides are based on the monomers making up the polyesteramides. The "p" stands for polymer; the "DTE" stands for Desaminotyrosyl Tyrosine Ethyl ester; the "succinate" refers to the identity of the dicarboxylic acid. p(DTE succinate) is formed by the polymerization of the tyrosine-derived monomer desaminotyrosyl tyrosine ethyl ester and the dicarboxylic acid succinic acid.

Another polyesteramide for use in the present invention contains three monomer subunits: desaminotyrosyl tyrosine Inclusion of a certain percentage of desaminotyrosyl tyrosine monomers in the polymer produces a polyesteramide with that certain percentage of free carboxylic acid groups in the pendant chains. The structure of the polyesteramide corresponding to p(DTE succinate) but having free carboxylic acid groups in the pendant chains can be represented by Formula 5.

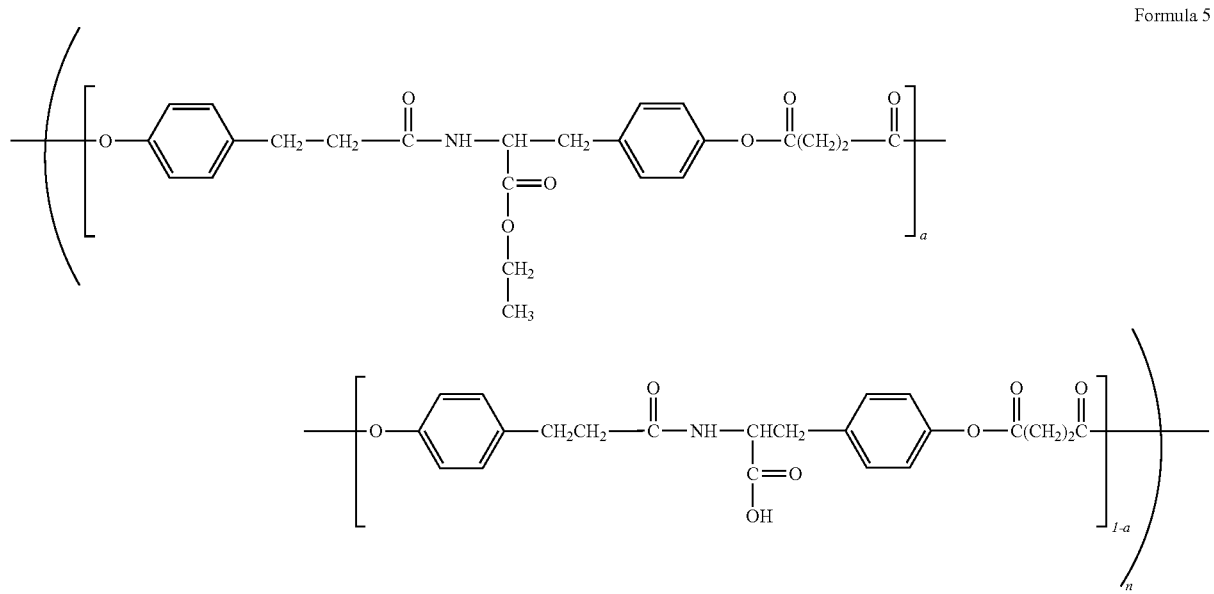

Formula 5

In Formula 5, or for any polymer having tyrosine-derived diphenol free acid moieties and tyrosine-derived diphenol ester moieties, "a" is a number between 0.01 and 0.99 that represents the mole fraction of tyrosine-derived monomer that is esterified, i.e., without a free carboxylic acid group. It is understood that the depiction of the tyrosine-derived monomers without and with free carboxylic acid groups as alternating in Formula 5 is for the sake of convenience only. Actually, the order in which tyrosine-derived monomers without free carboxylic acid groups and tyrosine-derived monomers with free carboxylic acid groups appear in the polyesteramide generally will be random, although the overall ratio in which these two monomers appear will be governed by the value of "a". Exemplary values of "a" include: 0.97, 0.96, 0.95, 0.94, 0.93, 0.92, 0.91, 0.90, 0.89, 0.88, 0.87, 0.86, 0.85, 0.84, 0.83, 0.82, 0.81, and 0.80, 0.75, 0.70, 0.65, 0.60 and 0.55. Ranges for "a" also include 0.95-0.60, 0.90-0.70, and 0.95-0.75

The presence of free carboxylic acid groups and percentage of these groups is indicated in the nomenclature used herein by modifying the name of the polyesteramide in the manner illustrated for p(DTE succinate) as follows: p(5% DT, DTE succinate) indicates p(DTE succinate) with 5% free carboxylic acid groups, p(10% DT, DTE succinate) indicates p(DTE succinate) with 10% free carboxylic acid groups, p(15% DT, DTE succinate) indicates p(DTE succinate) with 15% free carboxylic acid groups, etc.

Another polyesteramide for use in the present invention is p(DTE adipate). p(DTE adipate) is formed by the polymerization of the tyrosine-derived monomer desaminotyrosyl tyrosine ethyl ester and adipic acid. Another polyesteramide is p(DTE adipate) in which some of the pendant groups are free carboxylic acid groups, e.g., p(10% DT, DTE adipate), p(15% DT, DTE adipate), etc.

In general, any of the polyesteramides employed in the present invention can contain any desired percentage of pendant groups having free carboxylic acid groups. Thus, the present invention includes compositions of matter in which at least one antimicrobial agent is embedded, dispersed, or dissolved in a polyesteramide polymer matrix in which the polyesteramide polymer has the structure shown in Formulas 3 or 4 except that a certain percentage of the pendant chains are free carboxylic acid groups rather than esters. The structure of the polyesteramide polymer similar to Formula 3, but having free carboxylic acid groups in the pendant chains is shown in Formula 6.

Formula 6

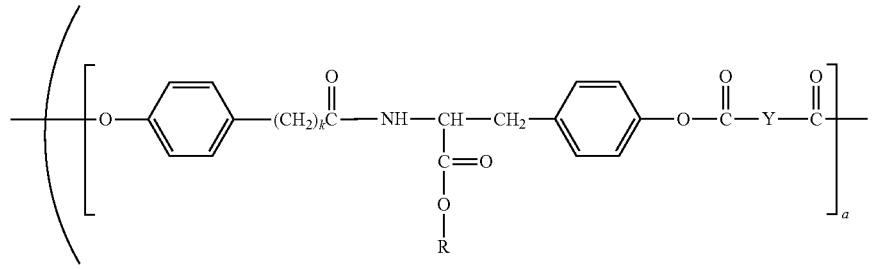

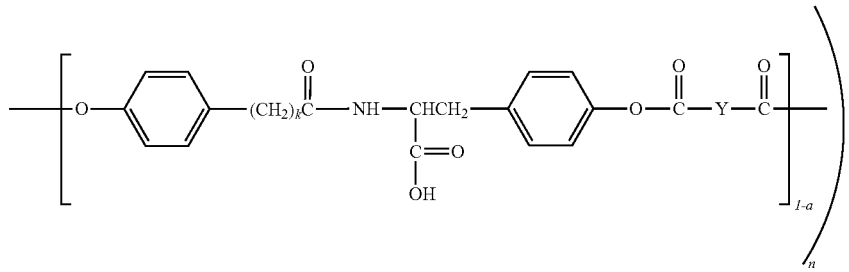

k = 1, 2

In Formula 6, R and Y are as in Formula 3. Usually, both instances of Y will be the same but this does not have to be the case. "a" is as defined above for Formula 5.

The structure of the polyesteramide polymer similar to Formula 4, but having free carboxylic acid groups in the pendant chains can be represented by Formula 7.

Formula 7

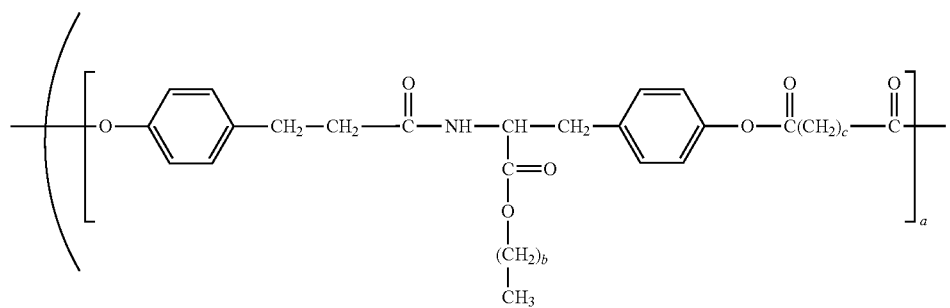

-continued

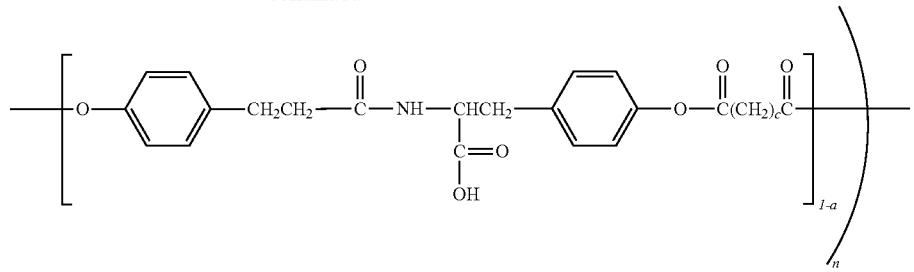

In Formula 7, "b" and "c" are as in Formula 3. Usually, both instances of "c" will be the same. Exemplary values of "b" include 1, 5, and 7; exemplary values of "c" include 2, 4, 6, and 8. Values of "a" are as defined in Formula 5.

quantity of the diphenol and the poly(alkylene oxide) is reacted with the dicarboxylic acid in a molar ratio of the diphenol to the poly(alkylene oxide) between about 1:99 and about 99:1 to give a polymer having the following structure:

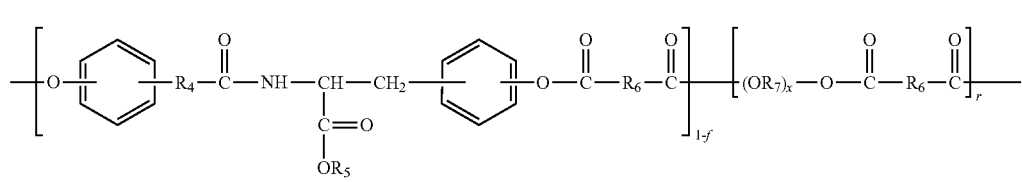

Formula 8

The incorporation of free carboxylic acid groups in the polyesteramides has the effect of accelerating the rate of polymer degradation and resorption when the polyesteramides are placed in physiological conditions, e.g., implanted into or applied to the body of a patient, as in a surgical incision site or a wound site. The presence of the free carboxylic acid groups also affects the behavior of the polyesteramide in response to pH. Polyesteramides having a relatively high concentration of pendent carboxylic acid groups are stable and water insoluble in acidic environments but dissolve or degrade rapidly when exposed to neutral or basic environments. By contrast, copolymers of low acid to ester ratios are more hydrophobic and will not degrade or resorb rapidly in either basic or acidic environments.

Such characteristics imparted by the carboxylic acid groups allow for the production of drug delivery devices including polyesteramides and at least one antimicrobial agent that is tailored to degrade or be resorbed at predetermined rates, and to deliver predetermined amounts of at least one antimicrobial agent at predetermined rates, by choosing the proper percentage of carboxylic acid groups in the polyesteramide. In particular embodiments, the percentage of pendant chains that are free carboxyl groups in the polyesteramide polymers used in the present invention is about 1-99%, 5-95%, 10-80%, 15-75%, 20-50%, or 25-40%. In particular embodiments, the percentage of pendant chains that are free carboxyl groups is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, or about 40%.

Further polymers that can be used in the present invention are co-polymers of the tyrosine-based polyesteramides described above and poly(alkylene oxides). Such co-polymers are described, e.g., in U.S. Patent Application Ser. No. 60/375,846 and U.S. Pat. Nos. 5,658,995 and 6,120,491. These co-polymers are random block copolymers of a dicarboxylic acid with a tyrosine-derived diphenol and a poly(alkylene oxide), in which an equimolar combined where $R_4$ is —CH—CH— or (—CH$_2$—); in which "j" is between 0 and 8, inclusive; $R_5$ is selected from the group consisting of straight and branched alkyl and alkylaryl groups containing up to 18 carbon atoms and optionally containing at least 1 ether linkage; $R_6$ is selected from the group consisting of saturated and unsaturated, substituted and unsubstituted alkylene, arylene and alkylarylene groups containing up to 18 carbon atoms; each $R_7$ is independently an alkylene group containing up to 4 carbon atoms; "x" is between about 5 and about 3,000; and "f" is the percent molar fraction of alkylene oxide in the copolymer and ranges between about 1 and about 99 mole percent.

In certain embodiments, $R_4$ is ethylene; $R_5$ is ethyl; $R_6$ is ethylene or butylene; $R_7$ is ethylene; and all substituents on the benzene rings in the polymer backbone are in the para position.

The poly(alkylene oxide) monomer used to produce the polymer shown in Formula 8 can be any commonly used alkylene oxide known in the art, for example a poly(ethylene oxide), poly(propylene oxide), or poly(tetramethylene oxide). Poly(alkylene oxide) blocks containing ethylene oxide, propylene oxide or tetramethylene oxide units in various combinations are also possible constituents within the context of the current invention.

In certain embodiments, the poly(alkylene oxide) can be a poly(ethylene oxide) in which "x" of Formula 8 is between about 10 and about 500, or about 20 and about 200. In certain embodiments, poly(ethylene oxide) blocks with a molecular weight of about 1,000 to about 20,000 g/mol are used.

Tyrosine-based polyesteramides also include polyesteramides that are formed from aminophenol esters, e.g., tyrosine esters and the like, and diacids in the manner described below. These polymers can incorporate both free acid side chains and esterified side chains. Exemplary tyrosine-based polyesteramides of this type include one or more repeating units represented by Formula 9

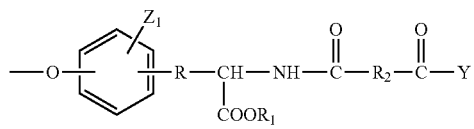

in which: R is $(CR_3R_4)_a$ or $—CR_3=CR_4—$; $R_1$ is hydrogen; saturated or unsaturated alkyl, aryl, alkylaryl or alkyl ether having from 1 to 20 carbon atoms; or $(R_5)_qO((CR_3R_4)_rO)_s$ $—R_6$; $R_2$ is independently a divalent, linear or branched, substituted or unsubstituted alkyl, alkenyl, alkynyl, aryl, alkylaryl, alkyl ether or aryl ether moiety having from 1 to 30 carbon atoms; $(R_5)O((CR_3R_4)_rO)_s(R_5)_q$; or $(R_5)_qCO_2$ $((CR_3R_4)_rO)_sCO(R_5)_q$; $R_3$ and $R_4$ are independently, hydrogen or linear or branched, substituted or unsubstituted alkyl having from 1 to 10 carbon atoms; $R_5$ is independently linear or branched, lower alkylene or lower alkenylene; $R_6$ is independently linear or branched, substituted or unsubstituted, saturated or unsaturated lower alkyl; the aromatic ring has from zero to four $Z_1$ substituents, each of which is independently selected from the group consisting of halide, lower alkyl, alkoxy, nitro, alkyl ether, a protected hydroxyl group, a protected amino group and a protected carboxylic acid group; Y is

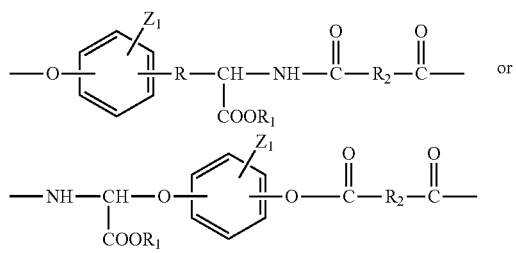

a is 0 to 10; each q is independently 1 to 4; each r is independently 1 to 4; and each s is independently 1 to 5000.

These polymers are biodegradable polymers having aminophenol units and diacid units that can be generally represented by the formula p(-AP—X—)$_n$, in which n is the actual number or the weight average number of repeat units in the polymer. In one embodiment, the aminophenols (AP) have the structure shown in Formula 10

Formula 10

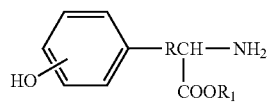

and the diacids (X) have the structure shown in Formula 11.

Formula 11

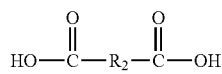

When these monomeric units are polymerized under condensation conditions (or other precursors depending on the synthesis route), the resultant polymers have backbones with both ester and amide bonds, and side chains with ester or free acids (depending on the choice of $R_1$). While the repeat motif of the polymer has the structure AP—X, this simple representation of the polymer does not reflect the various coupling permutations of the aminophenol and the diacid, i.e., whether the coupling between the aminophenol and the diacid occurs via reaction of the AP's amine functional group with one of the acid groups to produce an amide linkage or via the reaction of the AP's hydroxyl functional group with one of the acid groups to produce an ester linkage. Hence, the AP—X repeat unit can be represented by the either structure below ("repeat a" or "repeat b", respectively).

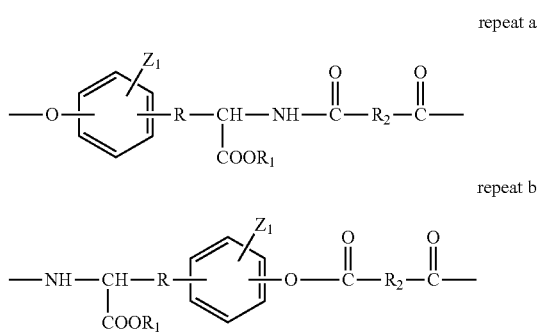

This simple structural representation (-AP—X—) does not show the relative relationship of these units to one another since these units can be further joined together by either an amide or ester bond. Hence, the actual structures of the polymers of the present invention which contain the aminophenol and diacid moieties described herein depend on the choice of synthetic route, the choice of coupling agents and the selective reactivity in forming amide or ester bonds.

Accordingly, these tyrosine-based polyesteramides are random copolymers of repeats a and b or strictly alternating copolymers of repeat a, repeat b or both repeats a and b, with the particular polymer structure determined by the method of synthesis as described herein.

Random copolymers of repeats a and b, are denominated by the simple formula p(-AP—X—), AP—X or as random ab polymers, such names being used interchangeably. Names for this polymer class are based on these representations so that random ab polymers are named for the aminophenol moiety followed by the diacid moiety, regardless of the starting materials. For example, a polymer made by random copolymerization of tyrosine ethyl ester (TE) as the aminophenol moiety with succinic acid as the diacid moiety is referred to as p(TE succinate) or TE succinate. If the diacid moiety were changed to glutaric acid, this random copolymer would be p(TE glutarate) or TE glutarate. For additional clarity or emphasis, the word random may be appended to the polymer name, e.g., TE succinate random or p(TE succinate) random. If the polymer is designated without anything after the name, then the polymer is a random copolymer.

There are two strictly alternating copolymers classes that can be obtained from these monomeric units: (1) a linear string of a single repeat, either "repeat a," thus in format $(a)_n$ or "repeat b," thus in format $(b)_n$, which are equivalent formats; or (2) a linear string of alternating "repeat a" and "repeat b," thus in form $(ab)_n$ or $(ba)_n$, which are equivalent representations for these polymers. In all cases, n is the number of repeat units. For polymers, n is usually calculated from the average molecular weight of the polymer divided by the molecular weight of the repeat unit.

Strictly alternating polymers of the (a)$_n$ form are referred to as p(-O-AP—X—) or as alternating "a" polymers. Alternating "a" polymers occur when the reaction conditions are such that the free amine of the aminophenol reacts first with the diacid (or other appropriate reagent) as controlled by the reaction conditions, forming an amide linkage and leaving the hydroxyl free for further reaction. For example, a polymer made by copolymerization of tyrosine ethyl ester (TE) as the aminophenol moiety with succinic anhydride (to provide the diacid moiety) leads to an alternating "a" polymer and is referred to herein as p(O-TE succinate) or O-TE succinate.

Polymers of the (ab)$_n$ form are referred to as p(-AP—X$_1$-AP—X$_2$—), p(AP—X$_1$-AP—X$_2$) or as AP—X$_1$-AP—X$_2$, when having "a" and "b" repeats with different diacids or as "p(-AP—X—) alternating" or as "AP—X alternating", when the "a" and "b" repeats have the same diacid.

Polymers with two different diacids can be made, for example, by reacting two equivalents of an aminophenol with one equivalent of a first diacid under conditions that favor amide bond formation and isolating the reaction product, a compound having the structure AP—X$_1$-AP, which is also referred to herein as a trimer because it consists of two aminophenol units and one diacid unit. This trimer is reacted with a second diacid under polymerization conditions to produce the polymer p(-AP—X$_1$-AP—X$_2$—) if the second diacid is different from the first diacid, or to produce the polymer p(-AP—X—) alternating if the second diacid is the same as the first diacid. As an illustration, an initial trimer made from TE and succinic acid is denominated as TE-succinate-TE. Reaction of TE-succinate-TE with glutaric acid acid produces the polymer p(TE-succinate-TE glutarate), whereas reaction with succinic acid produces the polymer p(TE succinate) alternating.

The polymers of the invention also include polymers made with mixed aminophenol repeats, mixed diacid repeats and mixed trimer repeats, or any combination of such mixtures. For these complex polymers, the mixed moiety is designated by placing a colon between the names of the two moieties and indicating the percentage of one of the moieties. For example, p(TE:10TBz succinate) random is a polymer made by using a mixture of 90% tyrosine ethyl ester and 10% tyrosine benzyl ester with an equimolar amount of the diacid succinic acid under random synthesis conditions. An example of a strictly alternating (ab)$_n$ polymer with a mixed second diacid is p(TE-diglycolate-TE 10PEG-bis-succinate:adipate). This polymer is made by preparing the TE-diglycolate-TE trimer and copolymerizing it with a mixture of 10% PEG-bis-succinic acid and 90% adipic acid. An example of a strictly alternating (ab)$_n$ polymer with mixed trimers is p(TE-succinate-TE:35TE-glutarate-TE succinate). This polymer is made by conducting a separate synthesis for each trimer, mixing the isolated trimers in the indicated ratio (65:35 succinate:glutarate) and copolymerizing with an equimolar amount of succinic acid. With such complexity, it is often simpler to list the various components and relative amounts in a table, especially for strictly alternating (ab)$_n$ polymers. Table 1 provides examples of some strictly alternating (ab)$_n$ polymers. In Table 1, T$_g$ is the glass transition temperature of the polymer after synthesis. Mol. Wt. is the molecular weight of the polymer after synthesis as determined by gel permeation chromatography.

Examples of tyrosine-based polyesteramides include, but are not limited to, those shown in Table 1 as well as polymers (1) wherein the aminophenol unit in the polymer is provided by a tyrosine ester such as tyrosine methyl ester, tyrosine ethyl ester, tyrosine benzyl ester, free tyrosine, or a methyl, ethyl, propyl or benzyl ester of 4-hydroxyphenyl-glycine as well as 4-hydroxyphenylglycine, and (2) wherein the diacid unit is succinic acid, glutaric acid, adipic acid, diglycolic acid, dioxaoctanoic acid, a PEG acid or a PEG bis-diacid (e.g., PEG-bis-succinate or PEG-bis-glutarate).

TABLE 1

| First Trimer AP-X$_1$-AP | % 1st | Second Trimer AP-X$_1$-AP | % 2d | First X$_2$ diacid | % 1st | Second X$_2$ diacid | % 2d | T$_g$ (° C.) | Mol. Wt. (kDa) |
|---|---|---|---|---|---|---|---|---|---|
| TE-diglycolate-TE | 100 | | | PEG600 Acid | 25 | Glutaric acid | 75 | 25 | 111 |
| TE-diglycolate-TE | 100 | | | PEG400-bis-succinate | 25 | Glutaric acid | 75 | 29 | 130 |
| TE-succinate-TE | 65 | TE-(PEG400-bis-succinate)-TE | 35 | Succinic acid | 100 | | | 32 | 120 |
| TE-glutarate-TE | 100 | | | PEG400-bis-succinate | 35 | Succinic acid | 65 | 28 | 190 |
| TE-glutarate-TE | 100 | | | PEG400-bis-succinate | 35 | Glutaric acid | 65 | 26 | 199 |
| TE-glutarate-TE | 100 | | | Glutaric acid | 100 | | | 70 | 74 |

For polymers with mixed aminophenol repeats, the polymer contains from about 5% to about 40% or from about 10% to about 30% of a first aminophenol repeat with the remainder being the second aminophenol repeat. For polymers with mixed diacid repeats, the polymer contains from about 10% to about 45% or from about 20% to about 40% of a first diacid repeat with the remainder being the second diacid repeat. For polymers with mixed trimer repeats, the polymer contains from about 5% to about 40% or from about 10% to about 30% of a first trimer with the remainder being the second trimer. Polymers made from any and all of the foregoing possible permutations are contemplated by the present invention. Additional examples of specific polymers of the invention include p(TE succinate), p(TE succinate) alternating, p(TE glutarate), p(TE glutarate) alternating, p(TE diglycolate), p(TE diglycolate) alternating, p(TE:15T glutarate), $T_g$ 78, Mol. wt. 74 kDa; and p(TE:15TBz glutarate). This last polymer is an example of an intermediate polymer used in preparation of p(TE:15T glutarate).

Other tyrosine-based polyesteramides include those in which a strictly alternating polymer has been synthesized with a trimer selected from the group consisting of TE-succinate-TE, TE-glutarate-TE, TE-adipate-TE, TE-diglycolate-TE, and TE-X-TE monomers wherein X is comprised of a PEG unit with or without other species, such as a PEG bifunctionalized via condensation with two equivalents of a diacid such as succinic acid, glutaric acid, adipic acid, diglycolic acid, or others. Any of these trimers can be copolymerized with a diacid repeat selected from the group of succinic acid, glutaric acid, adipic acid, diglycolic acid, dioxaoctandioic acid, a PEG acid and a PEG bis-diacid (e.g., PEG-bis-succinate and PEG-bis-glutarate), or any mixture of these diacids or other diacids.

Because of the bifunctionality of the aminophenol and the diacid, the basic monomeric unit (here arbitrarily designated as repeat a), can add either another of "repeat a" or add "repeat b" as the subsequent monomeric unit. Accordingly, the variable Y reflects this and is defined as "repeat a" with the amide bond (below left) or "repeat b" with the ester bond (below right).

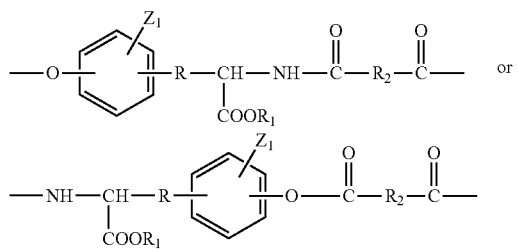

For a random polymer each subsequent Y would be randomly either "repeat a" or "repeat b." For a strictly alternating (a)$_n$ polymer, Y would always be "repeat a". For a strictly alternating (ab)$_n$ polymer, Y would always be "repeat b".

The values of each "a" are independently 0 or one of the whole numbers 1-10. When "a" is zero, the corresponding group is omitted and a single carbon bond is present. The value of each "q" and "r" is independently one of the whole numbers 1, 2, 3 or 4.

The value of each "s" is independently about 1 to about 5000 and determines the number of repeat units in the alkylene oxide chain. Hence, "s" can range from 1 or from 5 to about 10, to about 15, to about 20, to about 30, to about 40, to about 50, to about 75, to about 100, to about 200, to about 300, to about 500, to about 1000, to about 1500, to about 2000, to about 2500, to about 3000, to about 4000 and to about 5000. Additionally, when the length of the alkylene oxide chain is stated as a molecular weight, then "s" need not be a whole number but can also be expressed as a fractional value, representative of the average number of alkylene oxide repeating units based on the cited (or a measured) molecular weight of the poly(alkylene oxide).

The tyrosine-based polyesteramides can be homopolymers or copolymers. To create heteropolymers (or copolymers), as also described above in context of polymer nomenclature, mixtures of the aminophenol and/or the diacid (or appropriate starting materials) can be used to synthesize the polymers of the invention.

When the polymers are copolymers, they contain from at least about 0.01% to 100% of the repeating monomer units, from at least about 0.05%, 0.1%, 0.5%, 1%, 2%, 3%, 4%, 5%, 6%, 8%, 10%, 12%, 15% to about 30%, 40%, 50%, 60%, 75%, 90%, 95% or 99% in any combination of ranges. In certain embodiments, the range of repeating units in free acid form on the aminophenol moiety of the polymer is from about 5% to about 50%, i.e., $R_1$ is H-prepared via an intermediate in which $R_1$ is benzyl, with the remaining $R_1$ groups being alkyl or other ester stable to hydrogenolysis. In certain embodiments, the range of free acid is from about 5% to about 40%, including about 5%, about 10%, about 15%, about 20%, about 25%, about 30%, about 35%, and about 40%, inclusive of all ranges and subranges there between. In other embodiments, the free acid ranges from about 10% to about 15%, about 10% to about 20%, about 10% to about 25%, about 10% to about 30%, and about 10% to about 35%.

Alternatively or additionally, the copolymers can have varying ratios of the diacid moiety, so that mixtures have from about 20% to about 80% of at least one diacid described herein. In certain embodiments of the invention, the copolymers are a mixture of two or more diacids as described herein. In certain embodiments, mixed diacids are combinations of various alkylene oxide type moieties, such as PEG acids or PEG-bis-alkyl acids or combinations of those alkylene oxide type moieties with other diacids, especially small, and naturally-occurring, diacids such as succinic acid, glutaric acid, adipic acid and diglycolic acid. For alkylene oxide mixtures, the mixture contains from about 20%, 25%, 30%, 35%, 40%, 45% to about 50% of one alkylene oxide. In certain embodiments, the the mixture is about 50% of each alkylene oxide. For alkylene oxide-other diacid mixtures, the mixture contains from about 20%, 25%, 30%, 35%, 40%, 45% or 50% of the alkylene oxide, with the remainder being the other diacid. In yet another embodiment, the amount of the alkylene oxide is about 20% to about 40%.

Further, the ester moiety of the aminophenol can be varied by using alkyl esters or another class of esters such as alkylaryl esters, or esters with alkylene oxide chains or ether chains, or another compatible functional group. To have this ester moiety converted to a free acid, the polymer can be synthesized using a benzyl ester (or other easily hydrolyzable moiety) which can be removed by hydrogenolysis as described in U.S. Pat. No. 6,120,491 or by other technique that preferentially removes the benzyl group without hydrolyzing the backbone of the polymer. Hence, the polymers of the invention can be made with mixtures of aminophenol and diacids that have variability among the different substituents, i.e., differences can reside at any of R, $R_1$-$R_{10}$, $Z_1$ or the other variables of the repeat units. Finally, the other monomer units in the copolymer can be substantially different provided such moieties preserve the properties of the polymer and are capable of copolymerizing to form polymers with aminophenol and diacid moieties.

While many biodegradable tyrosine-derived polyesteramides are specifically illustrated above, further such polymers for use in the invention are described in U.S. Pat. Nos. 5,099,060; 5,216,115; 5,317,077; 5,587,507; 5,658,995; 5,670,602; 6,048,521; 6,120,491; 6,319,492; 6,475,477; 6,602,497; 6,852,308; 7,056,493; RE37,160E; and RE37,795E; as well as those described in U.S. patent application publication numbers 2002/0151668; 2003/0138488; 2003/0216307; 2004/0254334; 2005/0165203; 2009/0088548, 2010/0129417, 2010/0074940; those described in PCT publication numbers WO 99/52962; WO 01/49249; WO 01/49311; and WO03/091337; and those described in U.S. application Ser. No. 12/641,996.

The tyrosine-derived diphenol compounds used to produce the polyesteramides suitable for use in the present invention can be produced by known methods such as those described in, e.g., U.S. Pat. Nos. 5,099,060 and 5,216,115. The production of desaminotyrosyl tyrosine ethyl ester, desaminotyrosyl tyrosine hexyl ester, and desaminotyrosyl tyrosine octyl ester can also be carried out by known methods, see, e.g., Pulapura & Kohn, 1992, Biopolymers 32:411-417 and Pulapura et al., 1990, Biomaterials 11:666-678. The dicarboxylic acids are widely available from a variety of commercial sources.

A tyrosine-derived diphenol monomer and a dicarboxylic acid may be reacted to form a polyesteramide suitable for use in the present invention according to the methods disclosed in U.S. Pat. No. 5,216,115. According to these methods, the diphenol compounds are reacted with the dicarboxylic acids in a carbodiimide-mediated direct polyesterification using 4-(dimethylamino)pyridinium-p-toluene sulfonate (DPTS) as a catalyst to form the polyesteramides. Random block copolymers with poly(alkylene oxide) according to Formula 8 may be formed by substituting poly(alkylene oxide) for the tyrosine derived diphenol compound in an amount effective to provide the desired ratio of diphenol to poly(alkylene oxide) in the random block copolymer.

C-terminus protected alkyl and alkylaryl esters of tyrosine containing up to 8 carbon atoms can be prepared according to the procedure disclosed in J. P. Greenstein and M. Winitz, Chemistry of the Amino Acids, (John Wiley & Sons, New York 1961), p. 929. C-terminus protected alkyl and alkylaryl esters of tyrosine containing more than 8 carbon atoms can be prepared according to the procedure disclosed in U.S. Pat. No. 4,428,932.

N-terminus protected tyrosines can be prepared following standard procedures of peptide chemistry such as disclosed in Bodanszky, Practice of Peptide Synthesis (Springer-Verlag, New York, 1984).

Crude tyrosine derivatives are sometimes obtained as oils and can be purified by simple recrystallization. Crystallization of the pure product is accelerated by crystal seeding.

The diphenols can then be prepared by carbodiimide-mediated coupling reactions in the presence of hydroxybenzotriazide following standard procedures of peptide chemistry such as disclosed in Bodanszky, Practice of Peptide Synthesis (Springer-Verlag, New York, 1984) at page 145. The crude diphenols can be recrystallized twice, first from 50% acetic acid and water and then from a 20:20:1 ratio of ethyl acetate, hexane, and methanol, or, alternatively, by flash chromatography on silica gel, employing a 100:2 mixture of methylene chloride:methanol as the mobile phase. Desaminotyrosyl tyrosine esters also can be prepared by the carbodiimide mediated coupling of desaminotyrosine and tyrosine esters in the presence of hydroxybenzotriazole.

The diphenol compounds can then be reacted with dicarboxylic acids in a carbodiimide-mediated direct polyesterification using 4-(dimethylamino)pyridinium-p-toluene sulfonate (DPTS) as a catalyst to form polyesteramides.

Because the diphenols of the present invention are base-sensitive, the polyesteramides of the present invention are prepared by direct polyesterification, rather than by dicarboxylic acid chloride techniques. Polyesterification condensing agents and reaction conditions should be chosen that are compatible with the base-sensitive diphenol starting materials. Thus, the polyesteramides can also be prepared by the process disclosed by Ogata et al., 1981, Polym. J., 13:989-991 and Yasuda et al., 1983, J. Polym. Sci: Polym. Chem. Ed., 21:2609-2616 using triphenylphosphine as the condensing agent; the process of Tanaka et al., 1982, Polym. J. 14:643-648 using picryl chloride as the condensing agent; or by the process of Higashi et al., 1986, J. Polym. Sci: Polym. Chem. Ed. 24:589-594 using phosphorus oxychloride as the condensing agent with lithium chloride monohydrate as a catalyst.

The polyesteramides can also be prepared by the method disclosed by Higashi et al., 1983, J. Polym. Sci.: Polym. Chem. Ed. 21:3233-3239 using arylsulfonyl chloride as the condensing agent; by the process of Higashi et al., 1983, J. Polym. Sci.: Polym. Chem. Ed. 21:3241-3247 using diphenyl chlorophosphate as the condensing agent; by the process of Higashi et al., 1986, J. Polym. Sci.: Polym. Chem. Ed. 24:97-102 using thionyl chloride with pyridine as the condensing agent; or by the process of Elias, et al., 1981, Makromol. Chem. 182:681-686 using thionyl chloride with triethylamine. An additional polyesterification procedure is the method disclosed by Moore et al., 1990, Macromol. 23:65-70 utilizing carbodiimide coupling reagents as the condensing agents with the specially designed catalyst 4-(dimethylamino)pyridinium-p-toluene sulfonate (DPTS). A particular polyesterification technique modifies the method of Moore to utilize an excess of the carbodiimide coupling reagent. This produces aliphatic polyesteramides having molecular weights greater than those obtained by Moore. When carbodiimides are used in peptide synthesis as disclosed by Bodanszky, Practice of Peptide Synthesis (Springer-Verlag, New York, 1984), between 0.5 to 1.0 molar equivalents of carbodiimide reagent is used for each mole of carboxylic acid group present. In the preferred methods disclosed herein, greater than 1.0 molar equivalents of carbodiimide per mole of carboxylic acid group present are used. This is what is meant by describing the reaction mixture as containing an excess of carbodiiide.

Essentially any carbodiimide commonly used as a coupling reagent in peptide chemistry can be used as a condensing agent in the polyesterification process. Such carbodiimides are well-known and disclosed in Bodanszky, Practice of Peptide Synthesis (Springer-Verlag, New York, 1984) and include dicyclohexylcarbodiimide, diisopropylcarbodiimide, 1-(3-dimethylaminopropyl)-3-ethyl carbodiimide hydrochloride, N-cyclohexyl-N'-(2'-morpholinoethyl) carbodiimide-metho-p-toluene sulfonate, N-benzyl-N'-3'-dimethylaminopropyl-carbodiimide hydrochloride, 1-ethyl-3-(3-dimethylaminopropyl)carbodiimide methiodide, N-ethylcarbodiimide hydrochloride, and the like. In certain embodiments, the carbodiimides are dicyclohexyl carbodiimide and diisopropylcarbodiimide.

A reaction mixture is formed by contacting equimolar quantities of the diphenol and the dicarboxylic acid in a solvent for the diphenol and the dicarboxylic acid. Suitable solvents include methylene chloride, tetrahydrofuran, dimethylformamide, chloroform, carbon tetrachloride, and N-methyl pyrrolidinone. It is not necessary to bring all reagents into complete solution prior to initiating the polyesterification reaction, although the polymerization of slightly soluble monomers such as desaminotyrosyl tyrosine ethyl ester and succinic acid will yield higher molecular weight polymers when the amount of solvent is increased. The reaction mixture can also be heated gently to aid in the partial dissolution of the reactants.

The polymer molecular weight significantly increases as the amount of coupling reagent used is increased. The degree of molecular weight increase only begins to level off around four molar equivalents of carbodiimide per mole of carboxylic acid group. Increasing the amount of coupling reagent beyond four equivalents of carbodiimide has no further beneficial effect. While quantities of carbodiimide greater than four equivalents are not detrimental to the polyesterification reaction, such quantities are not cost-effective and are thus not favored for this reason.

Carbodiimide-mediated direct polyesterification can be performed in the presence of the catalyst 4-(dimethylamino) pyridinium-p-toluene sulfonate (DPTS). DPTS is prepared in accordance with the procedure of Moore et al., 1990, Macromol., 23:65-70. The amount of DPTS is not critical because the material is a true catalyst that is regenerated. The catalytically effective quantity is generally between about 0.1 and about 2.0 molar equivalents per mole of carboxylic acid group, and preferably about 0.5 equivalents per mole of carboxylic acid group.

The reaction proceeds at room temperature, or about 20-30° C. The reaction mixture can be heated slightly (<60° C.) prior to carbodiimide addition to partially solubilize less soluble monomers. However, the polymerization reaction itself should be conducted between 20° C. and 30° C. Within this temperature range, the reaction can be continued, with stirring, for at least 12 hours, and preferably for from one to four days. The polymer is recovered by quenching the reaction mixture in methanol, from which the polyesteramide usually precipitates while the residual reagents remain in solution. The precipitate may be separated by mechanical separations such as filtration and purified by solvent washing.

In a particular procedure, equimolar amounts of pure, dried tyrosine-derived diphenol and dicarboxylic acid are weighed and placed in a round-bottomed flask, pre-dried at 130° C. A suitable magnetic stir bar is placed into the flask. Then 0.4 equivalents of DPTS are added. The flask is fitted with a septum and flushed with nitrogen or argon to remove traces of moisture from the reaction mixture. Next, a quantity of HPLC grade methylene chloride is added via a syringe and the reaction mixture is stirred vigorously to suspend the reactants. The amount of methylene chloride used will depend upon the solubility of the diphenol, or the dicarboxylic acid, or both monomers. At this stage, the reaction mixture may be slightly heated to partially dissolve the monomers. While it is not essential that the monomers be completely dissolved, the quantity of solvent should be sufficient to dissolve the polymer as it forms and thus slowly bring the monomers into solution.

4.0 equivalents of diisopropylcarbodiimide are then added to the reaction mixture via a syringe. After about 10 minutes, the reaction mixture becomes clear, followed by the formation of a cloudy precipitate of diiospropylurea. After stirring between 20° C. and 30° C. for one to four days, the reaction is terminated by pouring the reaction mixture slowly and with vigorous stirring into ten volumes of IPA-methanol. The polymer precipitates while the residual reagents remain dissolved in methanol, resulting in the formation of the clear supernatant.

The polymeric product is retrieved by filtration and washed with large amounts of IPA-methanol to remove any impurities. If desired, the polymeric products can be further purified by dissolving in methylene chloride (10% or 20% w/w) and reprecipitating in IPA-methanol. The polymeric product is then dried to constant weight under high vacuum.

In order to make polyesteramides having free carboxylic acid groups in the pendant chains, it is not sufficient to simply use the above-described polymerization processes and include monomers having free carboxylic acid groups. This is because the free carboxylic acid groups would cross-react with the carbodiimide coupling reagents used in the above-described processes. Instead, the method described in U.S. Pat. No. 6,120,491, can be employed. In this method, a polyesteramide is synthesized, e.g., by the processes described above, with the inclusion of a monomer having a protecting group on the pendant chain that can be selectively removed after the polyesteramide is synthesized. This protecting group must be capable of being removed without significant degradation of the polymer backbone and without removal of ester groups from pendant chains at those positions where it is desired that free carboxylic acid groups not be present in the final polymer.

Another method uses benzyl esters as the protecting group. Thus, if it is desired to have a polyesteramide with a certain percentage of free carboxylic acid groups, then one would produce an intermediate step polyesteramide with that percentage of monomers having benzyl esters in their pendant chains. The benzyl esters are selectively removed by palladium-catalyzed hydrogenolysis in N,N-dimethylformamide (DMF) or similar solvents such as N,N-dimethylacetamide (DMA) and N-methylpyrrolidone (NMP) to form pendent carboxylic acid groups. Pure DMF, DMA, or NMP is necessary as the reaction solvent. The reaction medium must be anhydrous and the solvents have to be dried to ensure complete removal of all benzyl ester groups in the hydrogenolysis reaction. Essentially any palladium-based hydrogenolysis catalyst is suitable, and in certain methods, the palladium catalyst is palladium on barium sulfate. A level of palladium on barium sulfate between about 5% and about 10% by weight is used in certain embodiments. Certain methods also use 1,4-cyclohexadiene, a transfer hydrogenolysis reagent, in combination with hydrogen gas as a hydrogen source. The polymer starting material having pendent benzyl carboxylate groups can be dissolved in dimethylformamide at a solution concentration (w/v %) between about 5% and about 50%, or between about 10% and about 20%. For further details, see U.S. Pat. No. 6,120,491.

The co-polymers of tyrosine-based polyesteramides and poly(alkylene oxides) depicted in Formula 8 can be prepared by methods described in U.S. Pat. Nos. 6,048,521 and 6,120,491.

A method of synthesizing strictly alternating $(ab)_n$ polymers by synthesizing a trimeric diol and condensing that diol with a diacid to produce the desired polymers is shown below. The first step is done under conditions that favor amide bond formation over ester bond formation, for example by using a mild coupling agent. Hence, the monomers are reacted to produce the trimer:

HO-AP—$NH_2$+HO—C(O)—$R_{2a}$—C(O)—OH→HO-AP—NH—C(O)—$R_{2a}$—C(O)—NH-AP—OH.

The trimer can also be represented by the structure shown below:

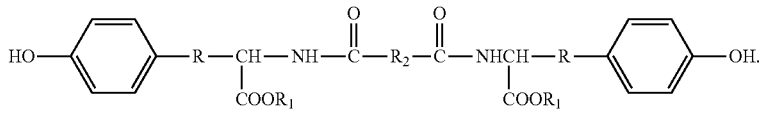

The trimer is purified and reacted with a second diacid, HO—C(O)—$R_{2b}$—C(O)OH, using a stronger coupling reagent to yield the strictly alternating repeat unit shown below:

[O-AP—NH—C(O)—$R_{2a}$—C(O)—NH-AP—O—C(O)—$R_{2b}$—C(O)]

Another method also produces strictly alternating polymers (ab)$_n$ polymers by first synthesizing a trimer with protected amines. This is accomplished by coupling an amine-protected aminophenol with a diacid, isolating the resultant trimer with protected amines at each end, deprotecting the amines and reacting with a second diol under condensation conditions. For example, HO-AP—NHPr and HO—C(O)—$R_{2a}$—C(O)OH are coupled to make PrHN-AP—O—C(O)—$R_{2a}$—C(O)—O-AP—NHPr, where Pr is a protecting group that can be removed in the presence of the ester bonds in the trimer and AP is a shorthand for the remainder of the aminophenol structure other than the hydroxyl and amine groups. After deprotection, a second diacid, HO—C(O)—$R_{2b}$—C(O)OH, is used to polymerize this trimer to form the strictly alternating (ab)n polymers.

Another method produces strictly alternating (a)$_n$ polymers by reacting the aminophenol with an anhydride to produce a dimer with free OH and free COOH groups as drawn in the exemplary reaction scheme below:

HO-AP—$NH_2$+$R_2$C(O)—O—C(O)—$R_{2a}$→HO-AP—NH—C(O)—$R_2$—COOH.

The reaction product is purified, more coupling reagent added to allow self condensation to proceed and produce a polymer with in which the diacid has an amide bond on one side and an ester bond on the other side as shown schematically below:

—(—O-AP—NH—C(O)—$R_2$—C(O)—)(—O-AP—NH—C(O)—$R_2$—C(O)—)(—O-AP—NH—C(O)—$R_2$—C(O)—)—.

Another synthesis method produces a random copolymer of the aminophenol and the diacid. In this method, equimolar amounts of each compound are reacted in the presence of a coupling reagent, and catalyst as described, for example, in U.S. Pat. Nos. 5,216,115; 5,317,077; 5,587,507; 5,670,602; 6,120,491; RE37,160E; and RE37,795E as well as in the literature, other patents and patent applications. Those of skill in the art can readily adapt these procedures to synthesize the polymers of the present invention. These polymers generally have low to moderate molecular weights (30-60 kDa).

The polymers and synthetic intermediates can be purified by those of skill in the art using routine methods, including extraction, precipitation, filtering, recrystallization and the like.

Examples of coupling agents for the methods described above include, but are not limited to, EDCI.HCl, DCC, DIPC in combination with DPTS, PPTS, DMAP. Suitable solvents include, but are not limited to methylene chloride, chloroform, 1,2-dichloroethane, either neat or in combination with lesser quantities of NMP or DMF.

In certain embodiments, the polyesteramides have weight-average molecular weights above about 40-50 kDa. In other embodiments, the weight-average molecular weight range is about 40 kDa to about 400 kDa; or about 25 kDa to about 150 kDa; or about 50-100 kDa. Molecular weights can be calculated from gel permeation chromatography (GPC) relative to polystyrene standards without further correction. The molecular weight of the polyesteramide polymer used in the present invention is a factor that the skilled artisan will consider when developing a polyesteramide/antimicrobial combination for a particular use. In general, keeping all other factors constant, the higher the molecular weight of the polymer, the slower will be the release rate of the antimicrobial agent.

Systematic variations in polyesteramide properties can be obtained by varying the nature of the pendant group attached to the C-terminus of the tyrosine-derived diphenol and the methylene groups in the dicarboxylic acid. One property that can be varied is the glass transition ($T_g$) temperature of the polyesteramide polymer. This is exemplified by the approximately 1° C. increments in the glass transition temperature observed in the series of polyesteramide polymers described in Brocchini et al., 1997, J. Amer. Chem. Soc. 119:4553-4554. In general, keeping all other factors constant, the higher the $T_g$ of the polymer, the slower will be the release rate of the antimicrobial agent. Therefore, one can vary the $T_g$ of the polyesteramide polymers, and thus the release rate of the antimicrobial agent, by adjusting the identity of the dicarboxylic acid and the pendant chain ester groups.

The polydispersity index (PDI) of the polyesteramides should be in the range of 1.5 to 4, for example, 1.8 to 3. Manipulating the polydispersity provides another way to adjust the release rate of the antimicrobial agent. Higher molecular weight polymers release the antimicrobial agent more slowly than lower molecular weight polymers. Thus, a batch of a particular polymer with an average molecular weight of 80 kDa and a PDI of 1.5 should release the antimicrobial agent more slowly than another batch of the same polymer with an average molecular of 80 kDa but a PDI of 3, since the second batch is more polydisperse and thus has more lower molecular weight components than the first batch.

The tyrosine-derived diphenol monomers and corresponding tyrosine-derived polyesteramides are biocompatible. The dicarboxylic acids generally are naturally occurring metabolites like adipic acid and succinic acid. Since the polyesteramides contain an ester linkage in the backbone, in certain embodiments, the polyesteramides are biodegradable and the degradation products, tyrosine, desaminotyrosine, and the dicarboxylic acids, all have known toxicity profiles.

Several members of the polyesteramides useful in the present invention were extensively tested in a variety of in vitro and in vivo assays and were found to exhibit excellent biocompatibility (Hooper et al., 1998, J. Biomed. Mat. Res. 41:443-454). In long-term in vivo studies, the present inventors have determined that the degradation products of the polyesteramides appear to be innocuous to surrounding tissue and promote ingrowth. In addition, surrounding tissue does not appear to exhibit inflammation in response to the polyesteramide degradation products. Implants in sheep, rabbits, dogs, and rats have demonstrated minimal tissue reaction and no local or systemic toxicity.

P22 Tyrosine-Derived Polyesteramides

The P22 family of tyrosine-derived polyesteramides is a subset of the tyrosine-derived polyesteramide family of polymers. The P22 family of polymers is synthesized by polymerizing a mixture of two phenolic monomers: desaminotyrosyl tyrosine ethyl ester (DTE) and desaminotyrosyl tyrosine (DT), protected as its benzyl ester, with succinic acid. The P22 family of polymers employs succinic acid; however, many different types of diacids have been used in the synthesis of tyrosine-derived polyesteramides. Varying the relative concentration of DTE to DT in the reaction mixture provides polymers with varied physicomechanical properties but identical degradation products. The molecular weights (MW) of the DTE and DT monomers are 357.40 Da and 329.35 Da respectively. Below is provided the general structure of the P22 Monomers (DTE: R=Ethyl; DT: R=Hydrogen):

An exemplary P22 tyrosine derived polyesteramide has the structure P22-27.5 (27.5% DT content; diacid=succinic acid).

Blends

The antimicrobial compositions of the invention also include blends of polymers. Accordingly, other polymers that can be blended with the tyrosine-derived polyesteramides described herein include, but are not limited to, polylactic acid, polyglycolic acid and copolymers and mixtures thereof such as poly(L-lactide) (PLLA), poly(D,L-lactide) (PLA,) polyglycolic acid [polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL) and poly(glycolide-co-caprolactone) (PGA/PCL); poly(oxa)esters, polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-

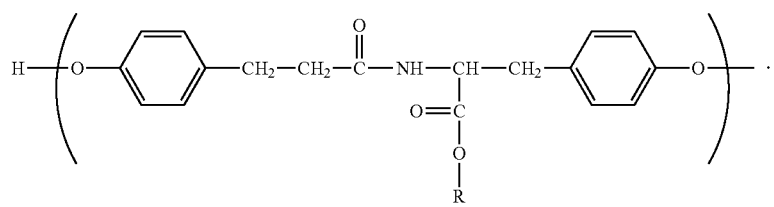

Formula 12

The polymer designation is dictated by the percentage of DT content relative to its esterified counterpart (i.e. DT to DTE ratio). For instance, 22-10 contains 10% DT and 90% DTE). A higher proportion of DT results in a more relatively hydrophilic polymer with a higher glass transition temperature. The polymers can be synthesized to molecular weights ranging from 10-130 kDa. Below is provided the general structure of the general structure of the P22 polymers (R=—CH$_2$—CH$_3$ for DTE or —H for DT):

butylacrylate, polyhydroxybutyrate (PHBT) and copolymers of polyhydroxybutyrate, poly(phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), other tyrosine-derived polyesteramides, other tyrosine-derived polycarbonates, other tyrosine-derived polyiminocarbonates, other tyrosine-derived polyphosphonates, polyethylene oxide, polyalkylene

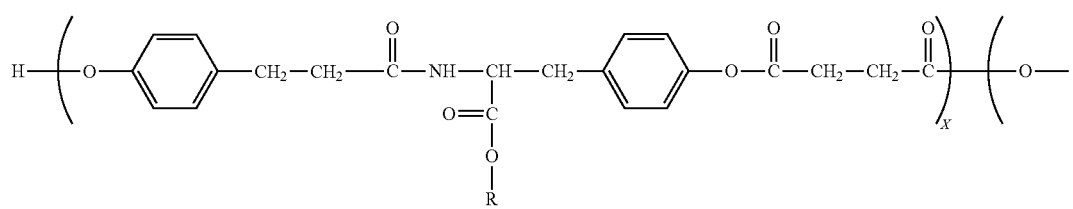

Formula 13

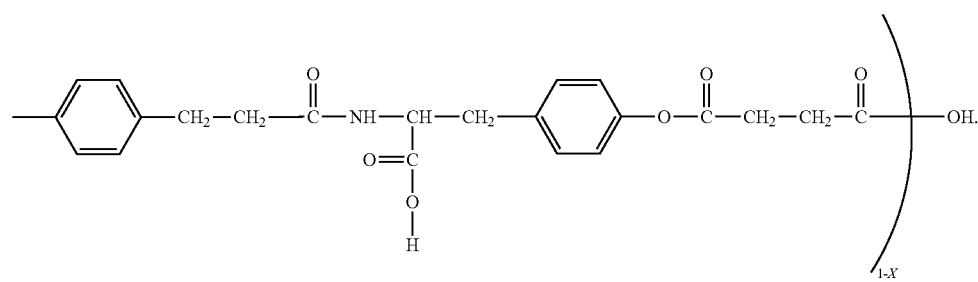

oxides, hydroxypropylmethylcellulose, polysaccharides such as hyaluronic acid, chitosan and regenerate cellulose, and proteins such as gelatin and collagen, and mixtures and copolymers thereof, among others as well as PEG derivatives or blends of any of the foregoing.

Commercially available polymers that can be blended with either the tyrosine-derived polesteramides or other polymers include Ostene®, a commercially available, water soluble surgical implant material which is composed of water soluble ethylene oxide and propylene oxide copolymers.

Using polymer blends provides many advantages, including the ability to make partially resorbable devices and fully resorbable devices that have varied resorption times for parts or all of the device. For example, a partially resorbable device may increase porosity over time and thus permit tissue in growth. Those of skill in the art can readily pick combinations of polymers to blend and determine the amounts of each polymer need in the blend to produce a particular product or achieve a particular result.

Osteoinductive and Osteoconductive Agents

In certain embodiments, the antimicrobial compositions of the invention further include one or more osteoinductive agents. Osteoinduction refers to the stimulation of bone formation. Any material that can induce the formation of ectopic bone in the soft tissue of an animal is considered osteoinductive. For example, most osteoinductive materials induce bone formation in athymic rats when assayed according to the method of Edwards et al. (Clinical Orthopeadics & Rel. Res. 357: 219-228, 1998). Osteoinductivity in some instances is considered to occur through cellular recruitment and induction of the recruited cells to an osteogenic phenotype. Osteoinductivity may also be determined in tissue culture as the ability to induce an osteogenic phenotype in culture cells (primary, secondary, or explants). Any osteoinductive agent known in the art may be used. Non-limiting examples of osteoinductive agents include bone morphogenetic protein, insulin growth factor, transforming growth factor beta, parathyroid hormone, demineralized bone, and angiogenic factors.

The osteoinductivity of a compound can be evaluated based on an osteoinductivity score as determined according to the method of Edwards et al. (Clinical Orthopeadics & Rel. Res. 357: 219-228, 1998). An osteoinductivity score refers to a score ranging from 0 to 4, in which a score of "0" represents no new bone formation; "1" represents 1% to 25% of implant involved in new bone formation; "2" represents 26% to 50% of implant involved in new bone formation; "3" represents 51% to 75% of implant involved in new bone formation; and "4" represents >75% of implant involved in new bone formation. In most instances, the score is assessed 28 days after implantation. However, the osteoinductive score may be obtained at earlier time points such as 7, 14, or 21 days following implantation.

In certain embodiments, the antimicrobial compositions of the invention further include one or more osteoconductive agents. Osteoconduction refers to the ability of a material to serve as a scaffold on which bone cells can attach, migrate, grow, and divide. Osteoconductive agents make it more likely for bone cells to fill the entire gap between two bone ends. They also serve as a spacer, which reduces the ability of tissue around the graft site from growing into the site. Any osteoconductive agent known in the art can be used. Non-limiting examples of such osteoconductive agents include human bone ("allograft bone"), purified collagen, calcium phosphate, hydroxyapatite, several calcium phosphate ceramics, and synthetic polymers. Some agents are reabsorbed by the body, while other agents may stay in the graft site for many years.

Degradation

The compositions of the invention herein may be partially or completely biodegradable. A biodegradable polymer refers to a polymer that has hydrolytically or oxidatively labile bonds or that is susceptible to enzymatic action or other in vivo breakdown process, or any combination thereof, under physiological conditions, which action leads to the degradation and/or breakdown, whether partial or complete, of the polymer. Polymers that are biodegradable have variable resorption times that depend, for example, on the nature and size of the breakdown products as well as other factors.

A resorbable polymer refers to a polymer (1) with repeating backbone units having at least some bonds that are unstable under physiological conditions, i.e., in the presence of water, enzymes or other cellular processes, the polymer is biodegradable and (2) the polymer as a whole or its degradation products are capable of being taken up and/or assimilated in vivo or under physiological conditions by any mechanism (including by absorption, solubilization, capillary action, osmosis, chemical action, enzymatic action, cellular action, dissolution, disintegration, erosion and the like, or any combination of these processes) in a subject on a physiologically-relevant time scale consonant with the intended biological use of the polymer.

The time scale of resorption depends upon the intended use. The polymers of the invention can be manipulated to provide for rapid resorption under physiological conditions, e.g., within a few days, to longer periods, such as weeks or months or years. Medically-relevant time periods depend upon the intended use and include, e.g., from 1-30 days, 30-180 days and from 1 to 24 months, as well as all time in between such as 5 days, 1, 2, 3, 4, 5 or 6 weeks, 2, 3, 4, 6 or months and the like. Accordingly, the present invention includes biocompatible, biodegradable putties capable of resorption under physiological condition on medically-relevant time scales, based on appropriate choice of polymers. Breakdown of the polymers can be assessed in a variety of ways using in vitro or in vivo methods known in the art.

Binders

Compositions of the invention can include a binder. An exemplary binder is polyethylene glycol (PEG; commercially available from Sigma-Aldrich, St. Louis, Mo.). The antimicrobial compositions can be formulated with any type of PEG, for example, PEG-200, PEG-300, PEG-400, PEG-600, PEG-1000, PEG-1450, PEG-3350, PEG-4000, PEG-6000, PEG-8000, PEG-20000, PEG-400-succinate, PEG-600-succinate, PEG-1000-succinate, etc. In particular embodiments, the percentage of PEG used in the antimicrobial compositions of the invention is about 1% to 99%, 5% to 95%, 10% to 80%, 15% to 75%, 30% to 70%, 20% to 50%, or 25% to 40%. In particular embodiments, the percentage of PEG used in the antimicrobial compositions is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45% 50%, 60%, 70% 80%, 90%, 95%, or 99%. Alternatively, the antimicrobial compositions can be formulated with a blend of different PEGs.

Other suitable binders include polypropylene glycols, and copolymers of polyethylene glycols and polypropylene glycols (e.g., block copolymers), for example those available under the trade name Pluronic® available from BASF.

Additional binders include, but are not limited to: art-recognized suspending agents, viscosity-producing agents, gel-forming agents and emulsifying agents. Other agents include those used to suspend ingredients for topical, oral or parental administration. Yet other candidates are agents useful as tablet binders, disintegrants or emulsion stabilizers. Still other candidates are agents used in cosmetics, toiletries and food products. Reference manuals such as the USP XXII-NF XVII (The Nineteen Ninety U.S. Pharmacopeia and the National Formulary (1990)) categorize and describe such agents.

Exemplary binders include resorbable macromolecules from biological or synthetic sources including sodium alginate, hyaluronic acid, cellulose derivatives such as alkylcelluloses including methylcellulose, carboxy methylcellulose, carboxy methylcellulose sodium, carboxy methylcellulose calcium or other salts, hydroxy alkylcelluloses including hydroxypropyl methylcellulose, hydroxybutyl methylcellulose, hydroxyethyl methylcellulose, hydroxyethyl cellulose, alkylhydroxyalkyl celluloses including methylhydroxyethyl cellulose, collagen, peptides, mucin, chrondroitin sulfate and the like.

Carboxymethylcellulose (CMC) sodium is another example of a binder. CMC is commercially available from suppliers such as, but not limited to: Hercules Inc., Aqualon® Division, Delaware; FMC Corporation, Pennsylvania; British Celanese, Ltd., United Kingdom; and Henkel KGaA, United Kingdom. Carboxymethylcellulose sodium is the sodium salt of a polycarboxymethyl ether of cellulose with a typical molecular weight ranging from 90,000-700,000. Various grades of carboxymethylcellulose sodium are commercially available which have differing viscosities. Viscosities of various grades of carboxymethylcellulose sodium are reported in Handbook of Pharmaceutical Excipients (2nd Edition), American Pharmaceutical Association & Royal Pharmaceutical Society of Great Britain. For example, low viscosity 50-200 cP, medium viscosity 400-800 cP, high viscosity 1500-3000 cP.

Aside from binders that are flowable at room temperature, binders also include reagents such as gelatin, which are solubilized in warm or hot aqueous solutions, and are transformed into a non-flowable gel upon cooling. The gelatin composition is formulated so that the composition is flowable at temperatures above the body temperature of the mammal for implant, but transitions to relatively non-flowable gel at or slightly above such body temperature.

In one embodiment, the binder of this invention is selected from a class of high molecular weight hydrogels including sodium hyaluronate (about 500-3000 kDa), chitosan (about 100-300 kDa), poloxamer (about 7-18 kD), and glycosaminoglycan (about 2000-3000 kDa). In certain embodiments, the glycosaminoglycan is N,O-carboxymethylchitosan glucosamine. Hydrogels are cross-linked hydrophilic polymers in the form of a gel which have a three-dimensional network. Hydrogel matrices can carry a net positive or net negative charge, or may be neutral. A typical net negative charged matrix is alginate. Hydrogels carrying a net positive charge may be typified by extracellular matrix components such as collagen and laminin. Examples of commercially available extracellular matrix components include Matrigel™ (Dulbecco's modified eagle's medium with 50.mu.g/ml gentamicin) and Vitrogen™ (a sterile solution of purified, pepsin-solubilized bovine dermal collagen dissolved in 0.012 N HCL). An example of a net neutral hydrogel is highly crosslinked polyethylene oxide, or polyvinylalcohol.

Pharmaceutical Formulations

As formulated with an appropriate pharmaceutically acceptable carrier in a desired dosage, the antimicrobial compositions herein can be administered to humans and other mammals topically. Non-limiting examples of dosage forms for topical administration of the antimicrobial compositions of the invention include putties, ointments, pastes, creams, lotions, foams, or gels. The active agent is admixed under sterile conditions with a pharmaceutically acceptable carrier and any needed preservatives or buffers as may be required. Preparations of such topical formulations are well described in the art of pharmaceutical formulations as exemplified, for example, by Remington's Pharmaceutical Sciences.

In certain embodiments, the antimicrobial composition is a putty. The putty is moldable, spreadable, stretchable, and biocompatible. To form the putty the following steps are performed: dry blend the components (i.e., at least one antimicrobial agent, an optional binder, and tyrosine-derived polyesteramide); and mix all components until the desired putty-like consistency is achieved.

In other embodiments, the antimicrobial composition is formulated as an ointment, a paste, a cream, or a gel. Ointments, pastes, creams, or gels may include the customary excipients, for example animal and vegetable fats, waxes, paraffins, starch, tragacanth, cellulose derivatives, silicones, bentonites, silica, talc, zinc oxide, or mixtures of these substances. The carrier or excipient thereof provides a base for the ointments, pastes, creams and gels. The antimicrobial compositions of the invention are added to the base, and the base and the antimicrobial compositions are kneaded together to generate the ointment, paste, cream, and gel formulations.

In certain embodiments, the compositions are formulated such that the antimicrobial agent is covalently bound to the polymer, e.g., a tyrosine-derived polyesteramide. In other embodiments, the composition is formulated such that the antimicrobial agent and the polymer, e.g., a tyrosine-derived polyesteramide, are combined in a non-covalent manner.

Uses

It has been found that the compositions of the invention are useful for preventing development of mediastinitis. In particular, the compositions of the invention can be formulated as a putty, paste, ointment/cream, gel, or foam and topically applied to an esophageal perforation in a subject or an incision site in a subject after the subject has undergone a median sternotomy, to prevent development of mediastinitis. The compositions of the present invention provide one or more of the antimicrobial agents described herein (e.g., rifampin and minocycline) in sufficient amounts to inhibit bacterial growth in the perforation or incision site, thereby preventing the development of mediastinitis (e.g., significantly reducing the incidence of mediastinitis in patients having an esophageal perforation, or in patients who have undergone median sternotomy).

Coronary artery bypass surgery (CABG) is one of the most common surgical procedures performed in the United States. Sternal wound infection (SWI) and mediastinitis are devastating complications associated with the prerequisite median sternotomy. Mediastinitis is an infection that results in swelling and irritation (inflammation) of the area between the lungs, i.e., the mediastinum. This area contains the heart, large blood vessels, windpipe (trachea), esophagus, thymus gland, lymph nodes, and connective tissues. Mediastinitis is a life-threatening condition with an extremely high mortality rate if recognized late or treated improperly.

Sternotomy wounds become infected in about 0.5% to about 9% of open-heart procedures and have an associated mortality rate of about 8% to about 15% despite flap closure. The rate of deep sternal wound infection (bone and mediastinitis) associated with median sternotomy ranges from between about 0.5% to about 5% and the associated mortality rate is as high as 22% independent of the type of surgery performed (Hollenbeak et al., Chest, 118:397-402, 2000). Infection of the sternum is most commonly attributed to contamination of the wound bed at the time of surgery or during the acute healing phase when the wound is still susceptible to bacteria (Hollenbeak et al. Infection Control and Hospital Epidemiology, 23(4):177, 2004; and Yokoe et al., Emerging Infectious Diseases, 10(11): 1924-1930, 2004).

After the CABG or other surgery has been completed, the sternum is usually closed with the assistance of wires or metal tapes. The sternal bony edges and gaps are subsequently covered and filled with a haemostatic agent. The most commonly used haemostatic agent is bone wax (bee's wax), despite the fact that bone wax has been reported to enhance infection, cause a foreign body reaction and inhibit bone growth. A median sternotomy is complicated by mediastinitis in about 1% to 2% of cases. Mortality for patients infected with mediastinitis after a median sternotomy is approximately 50%.

An esophageal perforation is a hole in the esophagus, the tube through which food passes from the mouth to the stomach. An esophageal perforation allows the contents of the esophagus to pass into the mediastinum, the surrounding area in the chest, and often results in infection of the mediastinum, i.e., mediastinitis. An esophageal perforation commonly results from injury during placement of a nasogastric tube or a medical procedure such as esophagoscopy or endoscopy.

The esophagus may also become perforated as the result of a tumor, gastric reflux with ulceration, violent vomiting, or swallowing a foreign object or caustic chemicals. Less common causes include injuries that hit the esophagus area (blunt trauma) and injury to the esophagus during an operation on another organ near the esophagus. Rare cases have also been associated with childbirth, defecation, seizures, heavy lifting, and forceful swallowing.

For patients with an early diagnosis and a surgery accomplished within 24 hours, the survival rate is 90%. However, this rate drops to about 50% when treatment is delayed.

Other causes of mediastinitis include perforations of the esophagus or from the contiguous spread of odontogenic or retropharyngeal infections. However, in modern practice, as discussed above, most cases of acute mediastinitis result from complications of cardiovascular or endoscopic surgical procedures. The compositions of the present invention are also useful for preventing or reducing the rate of mediastinitis caused by perforations in the esophagus or the spread of infections is described herein.

The compositions of the present invention are also useful as a replacement for haemostatic agents and bone wax, e.g. for covering bony edges and gaps after surgery.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Preparation of Polymer-Drug Powder

Tyrosine polyesteramide (P22-27.5) powder containing rifampin (10%) and minocycline (10%) drug was prepared by grinding polymer film. The polymer film containing rifampin and minocycline was prepared by solvent-cast method. Briefly, 8 g of tyrosine polyesteramide P22-27.5 was dissolved in 36 ml of THF. In a separate vial 1 g of rifampin and 1 g of minocycline was dissolved in 4 ml of methanol. The two solutions were mixed and poured into a TEFLON dish (10 cm diameter×1.9 cm depth). The solution was left at room temperature in a hood for 16-18 h to evaporate solvent. The dish was placed at 50° C. oven under vacuum for 24 h. The formulation bubbled up and formed a film. The film was crushed into the powder using a small mixer. The yield was 8.7 g Tyrosine polyesteramide polymer powder containing 10% each of rifampin and minocycline having MW range from 6 kDa to 70 000 kDa was prepared by this method. The MW weight of the polymer powder was assessed by GPC using against PEG standards.

Example 2: Preparation of PEG-Polymer Formulation

Various formulations were prepared in which P22-27.5-drug powder was combined with different ratios of PEG (MW 400) to yield various polymer-drug powder combinations. Table 2 below shows different combinations.

TABLE 2

| P22-27.5-rifampin-minocycline formulations with PEG 400 | | |
|---|---|---|
| # | P22-27.5-drug powder, g | PEG 400, g | % powder in PEG 400 |
| 1 | 0.3 | 5.7 | 5 |
| 2 | 0.3 | 2.7 | 10 |
| 3 | 0.3 | 1.7 | 15 |
| 4 | 0.3 | 1.0 | 23 |
| 5 | 6.25 | 16.9 | 27% |

Example 3: Viscosity Measurements

Viscosity of oil-like (lubricant type) formulation was measured on Brookfield viscometer (Model DV II+Pro, Brookfield Engineering Lab Inc., Middleboro, Mass.) equipped with temperature probe and 4 various spindles. The formulation #5 mentioned in Table 2 was taken into 20 ml scintillation vial and the viscosity was measured using spindle #63 at ambient conditions with a shear rate of 10 rpm. The viscosity of the formulation was 2230-2260 cp (centipoise).

Example 4: Putty Like Formulation

A putty like formulation was prepared by increasing the amount of P22-27.5-drug polymer in PEG 400. Such formulation has more percentage of tyrosine polyesteramide-drug powder (P227.5-rifampin and minocycline) and less of PEG 400.1 g of tyrosine polyesteramides-drug powder and 0.375 g of PEG 400 was found to form a suitable putty. In this putty like formulation, the PEG 400 percentage was 27.3% and the remaining percentage of the formulation was tyrosine polyesteramide-drug polymer.

The putty like formulation had a dough like nature. The putty, when handled with gloved finger (dry, non-powdered latex gloves), did not indicate fiber formation between surface of the putty (dough) and the glove as finger left the surface. The putty was observed to be malleable and hand moldable at ambient conditions.

Example 5: Preparation of Polyarylate and Ostene Formulations

Ostene® formulations containing tyrosine polyarylate (P22-27.5) polymer and rifampin (10%) and minocycline-.HCl (10%) drugs were prepared by the solvent-casting method. Briefly, Ostene® (CEREMED Inc., Lot # W2260408) and P22-27.5 were weighed into amber color 100 mL screw cap jars and dissolved in 18 mL of tetrahydrofuran (THF). To facilitate the dissolution the containers were placed in 37° C. incubator for ~2 h. In a separate 20 mL amber vial rifampin and minocycline.HCl were weighed out and dissolved in 2 mL of methanol. The two solutions were mixed and poured into Teflon® dishes (10 cm diameter×1.9 cm depth) and left at room temperature in hood for ~18 h to evaporate the solvent. The formulations were then dried at 60° C. under vacuum for 48 h. The weights of Ostene®, P22-27.5 polymer, and drugs used for preparing formulations are presented in Table 3. The yield was 2.3 g. It was observed that the original hand-molding nature of the Ostene® is maintained even after inclusion of tyrosine polyarylate polymer and drug. This is important to the hemostatic function of antibiotic bone wax products.

TABLE 3

Details of the component weights used for making Ostene ® formulations.

| Sample Id | Ostene ® (g) | P22-27.5 Polymer (g) | Rifampin (g) | Minocycline•HCl (g) |
|---|---|---|---|---|
| OS | 1.99945 | None | 0.24963 | 0.25033 |
| OS-10TP6 | 1.80443 | 0.19686 | 0.25047 | 0.25045 |
| OS-20TP6 | 1.59365 | 0.40543 | 0.25027 | 0.24995 |

Example 6: Characterization of Polyarylate and Ostene Formulations

GPC-MW

The MW of the Ostene® formulations was assessed by gel permeation chromatography (GPC) against PEG standards. The sample was dissolved in N,N-dimethyl formamide (DMF) (containing 0.1% TFA) at a concentration of 10-12 mg/mL. The MW data is presented in Table 4.

MW data of individual virgin samples is presented in Table 5. GPC chromatograms of the formulations (Table 4) showed multiple peaks. With addition of P22-27.5 polymer, polydispersity index (PDI) increased noticeably. The large PDI is due to the mixing of low and high MW polymers.

TABLE 4

GPC MW Data for Ostene ®-P22-27.5 Formulations.

| Sample Id | Mw | Mn | PDI | |
|---|---|---|---|---|
| OS | 14297 | 4836 | 2.96 | GPC showed multiple peaks |
| OS-10TP6 | 22107 | 5173 | 4.27 | GPC showed multiple peaks |
| OS-20TP6 | 29711 | 5693 | 5.22 | GPC showed multiple peaks |

TABLE 5

GPC MW Data for Ostene ® and P22-27.5 Polymer.

| Polymer | Mw | Mn | PDI | |
|---|---|---|---|---|
| Ostene ® | 20275 | 9296 | 2.18 | GPC showed Two major peaks |
| TPoly 6 (P22-27.5) | 111984 | 33234 | 3.37 | GPC showed Single Peak |

Thermal—Differential Scanning Calorimeter (DSC)

The Ostene® formulations were also characterized by Differential Scanning calorimeter (DSC) to check glass transition ($T_g$) temperature. Four (4)-six (6) mg of sample was subjected to a programmed two heating cycle method. Sample was heated from −50° C. to 200° C. at a rate of 10° C./minute. The $T_g$ temperatures were recorded in the $2^{nd}$ heating cycle. All formulations showed a prominent melting transition around 50° C. This is typical of PEG polymer transition.

Example 6: Drug Release from the Ostene® Formulations

Actual Loading of Rifampin and Minocycline in Ostene® Formulations

The drug content (loading) in each formulation was determined as per ATM 0421. A calibration plot was constructed for rifampin, minocycline by injecting standard solutions of known concentrations. A small portion of each formulation (approximately 20-35 mg) was dissolved in 5 ml of DMSO and, 50 ml of methanol was added. The solutions were mixed on a vortex and injected. The drug loading was determined as an average of three replicates (n=3).

The data is presented in Table 6. The actual rifampin loading was close 10%. Minocycline loading was 7.5%.

TABLE 6

Rifampin and minocycline estimation in the Ostene ® formulations (n = 3)

| Formulation | Rif. mg/mg of formulation | Mino. mg/mg of formulation |
|---|---|---|
| OS | 0.0939 | 0.0731 |
| | 0.0965 | 0.0759 |
| | 0.0963 | 0.0728 |

TABLE 6-continued

Rifampin and minocycline estimation in the Ostene ® formulations
(n = 3)

| Formulation | Rif. mg/mg of formulation | Mino. mg/mg of formulation |
|---|---|---|
| Average | 0.0955 | 0.0739 |
| S.D. | 0.0014 | 0.0017 |
| OS-10TP6 | 0.0892 | 0.0724 |
|  | 0.0970 | 0.0766 |
|  | 0.0999 | 0.0798 |
| Average | 0.0954 | 0.0763 |
| S.D. | 0.0056 | 0.0037 |
| OS-20TP6 | 0.0848 | 0.0680 |
|  | 0.0917 | 0.0676 |
|  | 0.0949 | 0.0725 |
| Average | 0.0905 | 0.0694 |
| S.D. | 0.0051 | 0.0027 |

Rifampin and Minocycline Release from Ostene® Formulations

Figure 2:
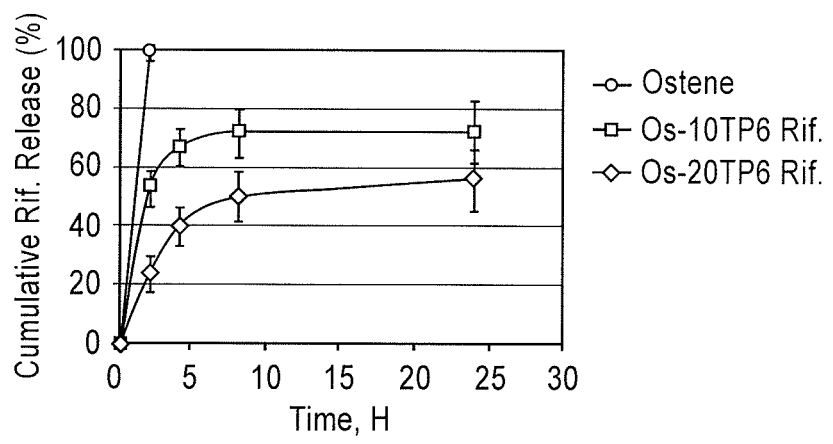
FIG. 2 illustrates the rate of rifampin release from Ostene® formulations.
Figure 3:
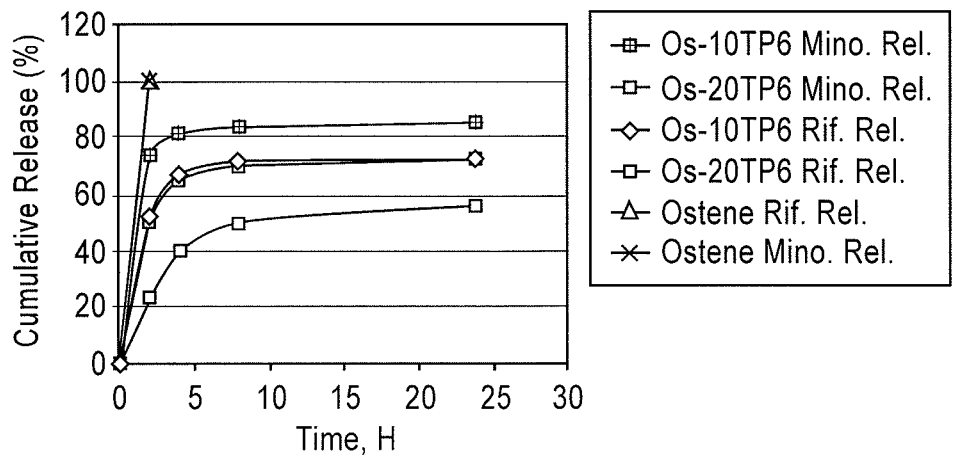
FIG. 3 illustrates the rate of minocycline and rifampin release from Ostene®-P22-27.5 matrix formulations.
Figure 4:
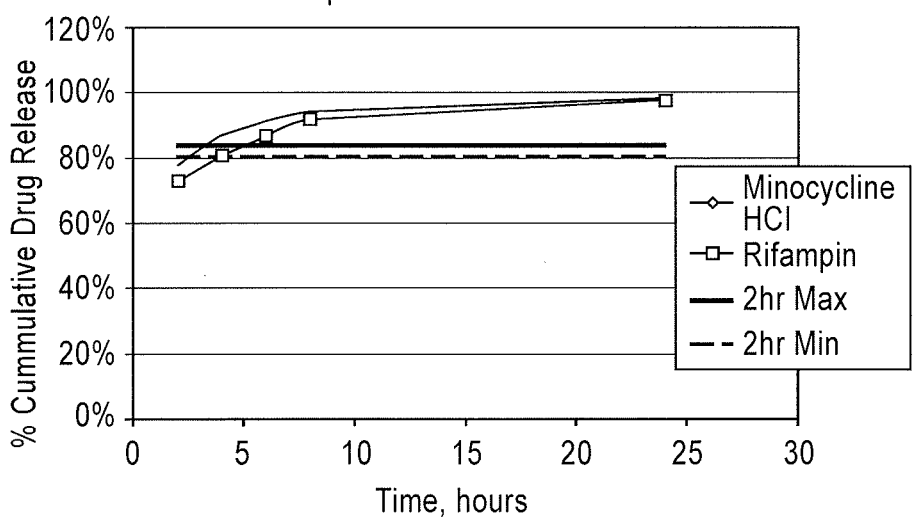
FIG. 4 illustrates the rate of minocycline and rifampin release from AIGIS® (TYRX Pharma, Inc.).

The release was studied as per ATM 0427. Briefly, known quantities of each formulation were weighed into 60 ml amber screw cap bottle. Twenty (20) ml of freshly prepared phosphate buffer saline (PBS 0.1 M, pH 7.4) was added and the bottles were placed in 37° C. incubator. The sample was with drawn and assayed by HPLC at 2, 4, 8 and 24 h time points. At each time, the entire PBS solution was replenished with fresh 20 ml PBS solution. The drug release from Ostene®, OS-10TP6 and OS-20TP6 matrices are presented in FIGS. 1 and 2 for minocycline and rifampin respectively. Each time points represents an average of three samples (n=3). Rifampin and minocycline release curves are presented in a single plot in FIG. 3. The release kinetics are strongly influenced by the inclusion of P22-27.5 tyrosine polyarylate polymer. About 75% of minocycline was released from OS-10TP6 matrix in first 2 h. This system has 10% (w/w) of P22-27.5 tyrosine polyarylate polymer. With the inclusion of 20% of P22-27.5 tyrosine polyarylate polymer only 51% of minocycline release was observed in first 2 h. At the end of 24 h, 86% and 73% of minocycline was released from OS-10TP6 and OS-20TP6 respectively. Higher percentage of P22-27.5 in the Ostene® matrix slows down the release of minocycline. A similar trend was observed in rifampin release. The amount of rifampin released however, was less than minocycline at corresponding time point. At 2 h time point the amount of rifampin released was 53 and 24% from OS-10TP6 and OS-20TP6 respectively. The rifampin release at 24 h was 73% and 56% for OS-10TP6 and OS-20TP6 respectively. Rifampin and minocycline release from Ostene® formulations was compared with AIGIS® devices presented in FIG. 4 (AIGIS®, available from TYRX, is an antibacterial envelope comprising a knitted polypropylene mesh substrate coated with a polyarylate resorbable polymer, containing rifampin and minocycline). The release profile shown by Ostene®-P22-27.5 systems is almost similar to that of AIGIS®.

Ostene® itself is a highly hydrophilic water soluble polymer. As a result, 100% of rifampin and minocycline were released from the Ostene® matrix (FIGS. 1 & 2) within the first 2 h. (Visual inspection indicates dissolution of Ostene® matrix. The HPLC indicates rifampin & minocycline peak area that is probably outside the linear range of calibration curve). Tyrosine polyarylate polymer P22-27.5 is a hydrophobic material. The release is mainly occurred by the diffusion mechanism. The inclusion of hydrophobic material in the hydrophilic Ostene® matrix slows down the water (buffer) uptake and therefore the rifampin and minocycline drug release.

What is claimed is:

1. A topical, antimicrobial composition comprising:
   poly(DTE-co-DT succinate),
   Ostene, and
   at least one antimicrobial agent,
   wherein the composition is formulated formulated as a malleable and hand-moldable hemostatic putty which functions as a bone wax substitute for covering bony edges and gaps after surgery.

2. The composition according to claim 1, wherein the antimicrobial agent comprises a combination of minocycline and rifampin.

3. The composition according to claim 1, wherein the composition is completely bioresorbable.

4. The composition according to claim 1, wherein the poly(DTE-co-DT succinate) ranges from about 30% to about 80% by total weight of the composition.

5. A topical, antimicrobial composition comprising:
   poly(DTE-co-DT succinate);
   Ostene; and
   an antibiotic,
   wherein the antibiotic is selected from the group consisting of tetracyclines, penicillins, macrolides, rifampin and combinations thereof, wherein the composition is formulated as a malleable and hand-moldable hemostatic putty configured which functions as a bone wax substitute for covering bony edges and gaps after surgery.

6. The composition according to claim 5, wherein the poly(DTE-co-DT succinate) ranges from about 30% to about 80% by total weight of the composition.

7. A topical, antimicrobial composition comprising:
   poly(DTE-co-DT succinate);
   Ostene;
   minocycline; and
   rifampin,
   wherein the composition is formulated as a malleable and hand-moldable hemostatic putty which functions as a bone wax substitute for covering bony edges and gaps after surgery.

8. The composition according to claim 7, wherein the poly(DTE-co-DT succinate) ranges from about 30% to about 80% by total weight of the composition.

9. The composition according to claim 1, wherein the antimicrobial agent comprises minocycline and rifampin, the composition being configured to release about 75% of the minocycline and about 50% of the rifampin within two hours.

10. The composition according to claim 1, wherein the antimicrobial agent comprises minocycline and rifampin, the composition being configured to release about 51% of the minocycline and about 24% of the rifampin within two hours.

11. The composition according to claim 1, wherein the antimicrobial agent comprises minocycline and rifampin, the composition being configured to release about 86% of the minocycline and about 73% of the rifampin within twenty four hours.

12. The composition according to claim 1, wherein the at least one antimicrobial agent is dispersed throughout the poly(DTE-co-DT succinate).

13. The composition according to claim 1, wherein the antimicrobial agent comprises minocycline and rifampin, the composition more rifampin by weight than minocycline.

14. The composition according to claim 1, wherein the structure of poly(DTE-co-DT succinate) is represented by the formula

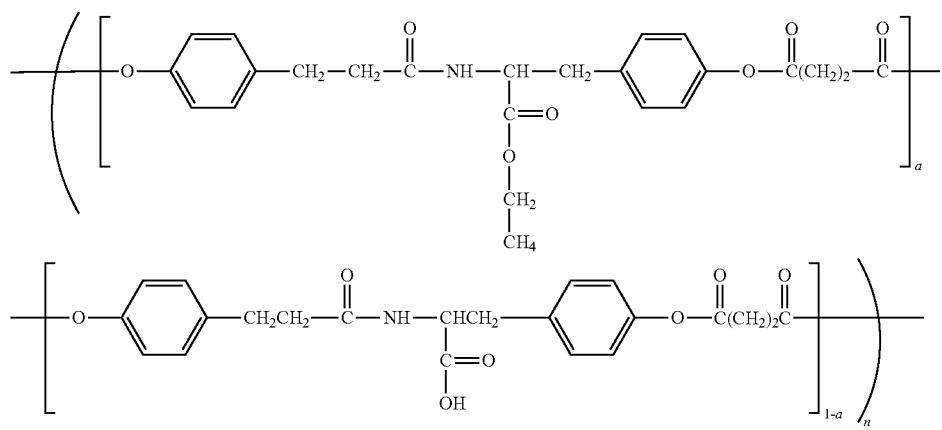

wherein "a" is a number between 0.01 and 0.99 that represents the mole fraction of tyrosine-derived monomer that is esterified and "n" is a number.

15. The composition according to claim 1, wherein the poly(DTE-co-DT succinate) comprises desaminotyrosyl tyrosine monomers.

16. The composition according to claim 1, wherein the composition comprises a greater amount of Ostene by weight than the poly(DTE-co-DT succinate).

17. The composition according to claim 1, wherein the composition comprises 10% w/w of the poly(DTE-co-DT succinate).

18. The composition according to claim 1, wherein the composition comprises a greater amount of the antimicrobial agent by weight than the poly(DTE-co-DT succinate).

* * * * *